United States Patent [19]

Woodruff

[11] Patent Number: 5,545,616
[45] Date of Patent: Aug. 13, 1996

[54] METHOD FOR PREDICTING AND/OR PREVENTING PRETERM LABOR

[75] Inventor: Teresa K. Woodruff, San Bruno, Calif.

[73] Assignee: Genentech, Inc., South San Francisco, Calif.

[21] Appl. No.: 310,609

[22] Filed: Sep. 22, 1994

[51] Int. Cl.⁶ ............................................. A61K 37/24
[52] U.S. Cl. ......................................... 514/8; 514/2
[58] Field of Search ................................ 514/8, 2

[56] References Cited

U.S. PATENT DOCUMENTS

| | | | |
|---|---|---|---|
| 4,624,944 | 11/1986 | Li et al. | 514/12 |
| 4,734,398 | 3/1988 | diZerega | 514/2 |
| 4,798,885 | 1/1989 | Mason et al. | |
| 4,997,815 | 3/1991 | Perrine et al. | 514/8 |
| 5,071,834 | 12/1991 | Burton et al. | |
| 5,102,868 | 4/1992 | Woodruff et al. | 514/2 |
| 5,166,190 | 11/1992 | Mather et al. | |
| 5,206,160 | 4/1993 | Takahashi et al. | |

FOREIGN PATENT DOCUMENTS

| | | |
|---|---|---|
| 210461A2 | 2/1987 | European Pat. Off. |
| WO91/10445 | 7/1991 | WIPO |
| WO92/20793 | 11/1992 | WIPO |
| WO94/19455 | 9/1994 | WIPO |

OTHER PUBLICATIONS

Adashi et al., "Antagonistic Interactions of Transforming Growth Factors in the Regulation of Granulosa Cell Differentiation" *Endocrinology* 119(4):1879–1881 (1986).

Attisano et al, "Identification of Human Activin and TGFβ Type I Receptors That Form Heteromeric Kinase Complexes with Type II Receptors" *Cell* 75:671–680 (Nov. 19, 1993).

Attisano et al., "Novel Activin Receptors: Distinct Genes and Alternative mRNA Splicing Generate a Repertoire of Serine/Threonine Kinase Receptors" *Cell* 68:97–108 (Jan. 10, 1992).

Baird et al., "Inhibin and related peptides in the regulation of reproduction" *Oxford Reviews of Reproductive Biology*, Milligan, S. R., New York, N.Y.:Oxford Univ. Press vol. 15:192–232 (1993).

Baly et al, "Development of a Specific and Sensitive Two–Site Enzyme–Linked Immunosorbent Assay for Measurement of Inhibin–A in Serum" *Endocrinology* 132(5):2099–2108 (1993).

Billestrup et al., "Inhibition of Somatotroph Growth Hormone Biosynthesis by Activin in Vitro" *Molecular Endocrinology* 4(2):356–362 (1990).

Brown et al., "Transforming Growth Factor–β: Role in Mediating Serum–Induced Endothelin Production by Vascular Endothelial Cells" *Endocrinology* 129(5):2355–2359 (1991).

Carson et al., "Growth factors in ovarian function" *J. Reprod. Fert.* 85:735–746 (1989).

deJong et al., "Evidence for inhibin–like activity in bovine follicular fluid" *Nature* 263:71–72 (Sep. 2, 1976).

deKretser et al, "The Isolation of Activin from Ovine Amniotic Fluid" *Endocrinology* 134(3):1231–1237 (1994).

deKretser et al., "Changes In Inhibin Levels in Reproductive States" *J. Endocrinol. Invest.* 117 (Abs. 14) (1988).

deKretser et al., "Recent advances in the human physiology of inhibin secretion" *J. Endocrinol. Invest.* 13:611–624 (1990).

dePaolo et al., "Follistatin and Activin: A Potential Intrinsic Regulatory System within Diverse Tissues" (43286A), Dept. of Molec. Endocrinol., La Jolla, CA:The Whittier Inst. for Diabetes and Endocrinol. pp. 500–512 (1991).

Derynck et al., "Human transforming growth factor–β complementary DNA sequence and expression in normal and transformed cells" *Nature* 316:701–705 (Aug. 22, 1985).

Ebner et al., "Cloning of a Type I TGF–β Receptor and Its Effect on TGF–β Binding to the Type II Receptor" *Science* 260:1344–1348 (May 28, 1993).

Estevez et al., "The daf–4 gene encodes a bone morphogenetic protein receptor controlling C. elegans dauer larva development" *Nature* 365:644–649 (Oct. 14, 1993).

Eto et al., "Purification and Characterization of Erythroid Differentiation Factor (EDF) Isolated from Human Leukemia Cell Line THP–1" *Biochem. and Biophy. Res. Comm.* 142(3):1095–1103 (Feb. 13, 1987).

Feng et al, "Transforming Growth Factor β Regulates the Inhibitory Actions of Epidermal Growth Factor during Granulosa Cell Differentiation" *The Journal of Biological Chemistry* 261(30):14167–14170 (Oct. 25, 1986).

Filicori, Marco MD, "Reproductive physiology: recent advances of clinical interest" *Current Opinion in Obstetrics and Gynecology* 3:309–315 (1991).

Fukuda et al., "Isolation of bovine follicular fluid inhibin of about 32 kDa" *Mol. and Cell. Endocrinology* 44:55–60 (1986).

Gonzalez–Manchon et al., "Activin–A, Inhibin and Transforming Growth Factor–β Modulate Growth of Two Gonadal Cell Lines" *Endocrinology* 125(3):1666–1672 (1989).

Hashimoto et al., "Activin/EDF as an Inhibitor of neural differentiation" *Biochem. and Biophy. Res. Comm.* 173(1):193–200 (Nov. 30, 1990).

Hedger et al., "Inhibin and activin regulate [3H] thymidine update by rat thymocytes and 3T3 cells in vitro" *Molec. and Cell. Endocrinology* 61:133–138 (1989).

(List continued on next page.)

Primary Examiner—James H. Reamer
Assistant Examiner—Keith MacMillan
Attorney, Agent, or Firm—Janet E. Hasak

[57] ABSTRACT

A method is provided for avoiding premature labor in a pregnant mammal comprising administering to said mammal, during labor, but before an infant is to be delivered, an effective amount of an activin antagonist. In one embodiment, the antagonist is follistatin. In another aspect a method is provided for assaying whether a pregnant mammal is in imminent delivery of its fetus in preterm labor comprising contacting a maternal serum sample or amniotic fluid sample of the mammal with a reagent that detects activin A and measuring the level of activin A in the serum or amniotic fluid. In addition, a kit for the assay is provided.

16 Claims, 6 Drawing Sheets

OTHER PUBLICATIONS

Higby et al., "Do tocolytic agents stop preterm labor? A critical and comprehensive review of efficacy and safety" *Am. J. Obstet Gynecol.* 168(4):1247–1259 (Apr. 1993).

Hutchinson et al., "Effects of Bovine Inhibin, Transforming Growth Factor–β and Bovine Activin–A on Granulosa Cell Differentiation" *Biochemical and Biophysical Res. Comm.* 146(3):1405–1412 (Aug. 14, 1987).

Iams, Jay D., "Curent Status of Prematurity Prevention" *Journal of the American Medical Assn.* 262(2):265–266 (Jul. 14, 1989).

Ignotz et al., "Transforming Growth Factor–β Stimulates the Expression of Fibronectin and Collagen and Their Incorporation into the Extracellular Matrix" *The Journal of Biological Chemistry* 261(9):4337–4345 (Mar. 25, 1986).

Jaffe et al *Reprod. Endocrinology*, Wonsiewicz, Martin, 3rd edition, W. B. Saunders Company pp. 758–769 (1991).

Kaiser et al, "The Rat Follistatin Gene is Highly Expressed in Decidual Tissue" *Endocrinology* 126(5):2768–2770 (1990).

Lee et al., "Interstitial Cell Cultures Secrete an Activity with Characteristics of the Inhibin β–β Homodimer, Activin" *The Molecular and Cellular Endocrinology of the Testis*, Cooke and Sharpe, Raven Press vol. 50:21–27 (1988).

Lee et al., "Secretion of Activin by Interstitial Cells in the Testis" *Science* 243:396–398 (1988).

Ling et al., "Isolation and Characterization of Gonadal Polypeptides that Regulate the Secretion of Follicle Stimulating Hormone" *Nonsteroidal Gonadal Factors: Physiological Roles and Possibilities in Contraceptive Development*, Conrad Int'l Workshop, Norfolk, Virginia vol. 3:30–46 (Jan. 6, 1988).

Ling et al., "Isolation and partial characterization of a Mr 32,000 protein with inhibin activity from porcine follicular fluid" *Proc. Natl. Acad. Sci. USA* 82:7217–7221 (1985).

Ling et al., "Pituitary FSH is released by a heterodimer of the β–subunits from the two forms of inhibin" *Nature* 321:779–782 (Jun. 19, 1986).

Lopez–Bernal et al., "Prostaglandins, chorioamnionitis and preterm labour" *British Journal of Obstetrics and Gynaecology* 94:1156–1158 (Dec. 1987).

Manova et al., "Expression of activins and TGFβ1 and β2 RNAs in early postimplantation mouse embryos and uterine decidua" *Mechanisms of Development* 36:141–152 (1992).

Mason et al., "Acivin B: Precursor Sequence Genomic Structure and in Vitro Activities" *Molecular Endocrinolgy* 3(9):1352–1358 (1989).

Mason et al., "Structure and Recombinant Expression in Mammalian Cells" *Inhibin–Non–steroidal Regulation of Follicle Stimulating Hormone Secretion*, Burger et al., Serono Symposium, Chapter Human InhibinActivin, vol. 42:77–88 (1987).

Mason et al., "Structure of two human ovarian inhibins" *Biochem. and Biophys. Res. Comm.* 135(3):957–964 (Mar. 28, 1986).

Mather et al., "Activin Stimulates Spermatogonial Proliferation in Germ–Sertoli Cell Cocultures from Immature Rat Testis" *Endocrinology* 127(6):3206–3214 (1990).

Mathews et al., "Expression Cloning of an Activin Receptor, a Predicted Transmembrane Serine Kinase" *Cell* 65:973–982 (Jun. 14, 1991).

Matsuzaki et al., "A Widely Expressed Transmembrane Serine/Threonine Kinase That Does Not Bind Activin, Inhibin, Transforming Growth Factor β, or Bone Morphogenic Factor" *J. Biolog. Chem.* 268(17):12719–12723 (Jun. 15, 1993).

McLean et al., "Prediction and Early Diagnosis of Preterm Labor: A Critical Review" *Obstetrical and Gynecological Survey* 48(4):209–225 (1993).

Mercado et al, "Effects of Estrous Cycle Stage and Pregnancy on Follistatin Gene Expression and Immunoreactivity in Rat Reproductive Tissues: Progesterone is Implicated in Regulating Uterine Gene Expression" *Endocrinology* 132(4):1774–1781 (1993).

Meunier et al., "Gonadal and extragonadal expression of onhibin α, βA, and βB subunits in various tissues predicts diverse functions" *Proc. Natl. Acad. Sci. USA* 85:247–251 (Jan. 1988).

Minami et al., "Immunohistochemical Localiztion of Inhibin/Activin Subunits in Human Placenta" *Obstetrics & Gynecology* 80(3, Part 1):410–414 (Sep. 1992).

Mine et al., "Pertussis Toxin Blocks Activin A–induced Production of Inositol Phosphates in Rat Hepatocytes" *Biochem. and Biophy. Research Comm.* 186(1):205–210 (Jul. 15, 1992).

Mine et al., "Stimulation of Glucose Production by Activin–A in Isolated Rat Hepatocytes" *Endocrinology* 125(2):586–591 (1989).

Mitrani et al., "Activin Can Induce the Formation of Axial Structures and Is Expressed in the Hypoblast of the Chick" *Cell* 63:495–501 (Nov. 2, 1990).

Mondschein et al., "Effects of Transforming Growth Factor–β on the Production of Immunoreactive Insulin–Like Growth Factor I and Progesterone and on [3H]Thymidine Incorporation in Porcine Granulosa Cell Cultures" *Endocrinology* 123(4):1970–1976 (1988).

Murata et al., "Erythroid differentiation factor is encoded by the same mRNA as that of the inhibin βA chain" *Proc. Natl. Acad. Sci. USA* 85:2434–2438 (Apr. 1988).

Nakamura et al., "Isolation and Characterization of Native Activin B" *The Journal of Biol. Chem.* 267(23):16385–16389 (Aug. 15, 1992).Norman et al., "Inhibin and relaxin concentrations in early singleton, multiple, and failing pregnancy: relationship to gonadotropin and steroid profiles" *Fertility and Sterility* 59(1):130–137 (Jan. 1993).

Peng et al, "Expression of the Type II Activin Receptor Gene in the Human Placenta" *Endocrinology* 133(6):3046–3049 (1993).

Penschow et al, "Differential expression of inhibin ξ and βA subunit genes in rat and mouse ovarian follicles during pregnancy"*Jour. Molec. Endocrinol.* 4:247–255 (1990).

Petersen et al, "Serum relaxin as a potential marker for preterm labour" *Brit. J. of Obstet. and Gynaecology* 99:292–295 (Apr. 1992).

Petraglia et al., "Activin A and activin B measured in maternal serum, cord blood serum and amniotic fluid during human pregnancy"*Endocrine Journal* 1:323–327 (1993).

Petraglia et al., "Activin at Parturition: Changes of Maternal Serum Levels and Evidence for Binding Sites in Placenta and Fetal Membranes"*Obstetrics & Gynecology* 84(2):278–282 (Aug. 1994).

Petraglia et al., "Gonadotropin–Releasing Hormone, Inbibin, and Activin in Human Placenta: Evidence for a Common Cellular Localization"*Jour. Clin. Endocrin. and Metabolism* 74(5):1184–1188 (1992).

Petraglia et al., "Inhibin and Activin in Human Fetal Membranes: Evidence for a Local Effect on Prostaglandin Release" *Journ. Clin. Endocrin. and Metabolism* 77(2):542–548 (1993).

Petraglia et al., "Inhibin and activin modulate the release of gonadotropin–releasing hormone, human chorionic gonadotropin, and progesterone from cultured human placental cells" *Proc. Natl. Acad. Sci. USA* 86:5114–5117 (Jul. 1989).

Petraglia et al., "Inhibin subunits in human placenta: Localization and messenger ribonucleic acid levels during pregnancy" *Am. J. Obstet. Gynecol.* 165(3):750–758 (Sep. 1991).

Petraglia et al., "Local Production and Action of Follistatin in Human Placenta" *Journ. of Clin. Endocrinol. and Metabolism* 78(1):205–210 (1994).

Petraglia et al., "Localization, Secretion, and Action of Inhibin in Human Placenta" *Science* 237:187–189 (Jul. 1987).

Petraglia et al., "Maternal decidua and fetal membranes contain immunoreactive neuropeptide Y" *J. Endocrinol. Invest.* 16:201–205 (1993).

Petraglia et al., "Presence and Synthesis of Inhibin Subunits in Human Decidua" *Journ. Clin. Endocrin. and Metabolism* 71(2):487–492 (1990).

Petraglia et al., "Sources and actions of inhibin and activin in pregnancy" *Hormones in Gunecological Endocrinology*, Genazzani and Petraglia, New Jersey:The Parthenon Publishing Group pp. 269–277 (Feb. 1992).

Petraglia, Felice, "Placental neurohormones: secretion and physiological implications" *Molecular and Cellular Endocrin.* 78:C109–C112 (1991).

Plotsky et al., "Central Activin Administration Modulates Corticotropin–Releasing Hormone and Adrenocorticotropin Secretion" *Endocrinology* 128(5):2520–2525 (1991).

Qu et al., "Changes in Bioactive and Immunoactive Inhibin Levels around Human Labor" *Journ. of Clin. Endocrinol. and Metabolism* 74(6):1290–1295 (1992).

Rabinovici et al., "Localization and Regulation of the Activin–A Dimer in Human Placental Cells" *Journ. Clin. Endocrin. and Metabolism* 75(2):571–576 (1992).

Rivier et al., "Effect of Recombinant Activin–A on Gonadotropin Secretion in the Female Rat" *Endocrinology* 129(5):2463–2465 (1991).

Rivier et al., "Purification and Partial Characterization of Inhibin From Porcine Follicular Fluid" *Biochem. and Biophys. Res. Comm.* 133(1):120–127 (Nov. 27, 1985).

Roberts et al, "Expression of Messenger Ribonucleic Acids Encoding the Inhibin/Activin System during Mid– and Late–Gestation Rat Embryogenesis" *Endocrinology* 134(2):914–923 (1994).

Roberts et al., "Expression of Inhibin/Activin Subunit Messenger Ribonucleic Acids during Rat Embryogenesis" *Endocrinology* 128(6):3122–3128 (1991).

Robertson et al., "The Isolation of Polypeptides With FSH Suppressing Activity From Bovine Follicular Fluid Which Are Structurally Different to Inhibin" *Biochem. and Biophysical Res. Comm.* 149(2):744–749 (Dec. 16, 1987).

Romero et al, "Infection and Preterm Labor" *Clinical Obsterics and Gynecology* 31(3):553–584 (Sep. 1988).

Romero et al., "The diagnostic and prognostic value ofamniotic fluid white blood cell count, glucose, interleukin–6, and Gram stain in patients with preterm labor and intact membranes" *Am. J. Obstet. Gynecol.* 169(4):805–816 (Oct. 1993).

Romero et al., "Interleukin–1: A signal for the onset of parturition" *Am. J. Obstet. Gynecol.*, Chapter Infection and Labor, 160(5, Pt. 1):1117–1123 (May 1989).

Romero et al., "Tumor necrosis factor in preterm and term labor" *Am. J. Obstet. Gynecol.* 166(5):1576–1587 (May 1992).

Sawchenko et al., "Inhibin β in Central Neural Pathways Involved in the Control of Oxytocin Secretion" *Nature* 334:615–617 (Aug. 18, 1988).

Schneyer et al., "Immunoreactive Inhibin α–Subunit in Human Serum: Implications for Radioimmunoassay" *Journ. of Clin. Endocrinol. and Metabolism* 70(4):1208–1212 (1990).

Schubert et al., "Activin is a nerve cell survival molecule"*Nature* 344:868–870 (Apr. 26, 1990).

Schwall et al., "Multiple Actions of Recombinant Activin–A in Vivo" *Endocrinology* 125(3):1420–1423 (1989).

Schwall et al., "Recombinant Expression and Characterization of Human Activin A" *Molec. Endocrinology* 2(12):1237–1242 (1988).

Schwartz et al., "Evidence for ovarian inhibin: Suppression of the secondary rise in serum foll icle stimulating hormone levels in proestrous rats by injection of por licular fluid" *Proc. Natl. Acad. Sci. USA* 74(12):5721–5724 (Dec. 1977) 12:5721–5724 (Dec. 1977).

Shi et al, "Regulation of Human Chorionic Gonadotropin Secretion and Messenger Ribonucleic Acid Levels by Follistatin in the NUCC–3 Choriocarcinoma Cell Line" *Endocrinology* 134(6):2431–2437 (1994).

Smith et al., "Identification of a potent Xenopus mesoderm–inducing factor as a homologue of activin A" *Nature* 345:729–731 (Jun. 21, 1990).

Smith et al., "Predictive Value of Uterine Contractility and the Serum Levels of Progesterone and Oestrogens with Regard to Preterm Labour" *Gynecol. Obstet. Invest.* 18:252–263 (1984).

Spencer et al., "Human Recombinant Activin–A Inhibits Proliferation of Human Fetal Adrenal Cells In Vitro" *Journ. of Clin. Endocrinol. and Metabolism* 71:710 (1990).

Steele et al, "Acute Stimulation of Human Chorionic Gonadotropin Secretion by Recombinant Human Activin–A in First Trimester Human Trophoblast" *Endocrinology* 133(1):297–303 (1993).

Sugino et al., "Erythroid Differentiation Factor Can Modulate Follicular Granulosa Cell Functions" *Biochem. and Biophys. Res. Comm.* 153(1):281–288 (May 31, 1988).

Tanimoto et al., "Regulation of activin βA mRNA level by cAMP" *Biochem. and Biophys. Res. Comm.* 82(2):773–778 (Jan. 31, 1992).

ten Dijke, et al., "Activin receptor–like kinases: a novel subclass of cell–surface receptors with predicted serine/threonine kinase activity" *Oncogene* 8:2879–2887 (1993).

Thomsen et al., "Activins Are Expressed Early in Xenopus Embryogenesis and Can Induce Axial Mesoderm and Anterior Structures" *Cell* 63:485–493 (Nov. 2, 1990).

Torney et al., "Characterization of inhibin and related proteins in bovine fetal testicular and ovarian extracts: evidence for the presence of inhibin subunit products and FSH–suppressing protein" *Journ. of Endocrinology* 133:111–120 (1992).

Totsuka et al., "A Novel Action of Activin A: Stimulation of Insulin Secretion in Rat Pancreatic Islets" *Biochem. and Biophys. Res. Comm.* 156(1):335–339 (Oct. 14, 1988).

Tuuri et al., "The Tissue Distribution of Activin βA—βB–Subunit and Follistatin Messenger Ribonucleic Acids Suggests Multiple Sites of Action for the Activin–Follistatin System during Human Development" *Journ. of Clin. Endocrinol. and Metabolism* 78(6): 1521–1524 (1994).

Ueno et al., "Isolation and Partial Characterization of Follistatin: A Single–Chain Mr 35,000 Monomeric Protein that Inhibits the Release of Follicle–Stimulating Hormone" *Proc. Natl. Acad. Sci. USA* 84:8282–8286 (1987).

Vale et al., "Chemical and Biological Characterization of the Inhibin Family of Protein Hormones" *Recent Progress in Hormone Research* 44:1–34 (1988).

Vale et al., "Purification and characterization of an FSH releasing protein from porcine ovarian follicular fluid" *Nature* 321:776–779 (Jun. 19, 1986).

van den Eijnden et al., "Activin–like factor from a Xenopus laevis cell line responsible for mesoderm induction" *Nature* 345:732–734 (Jun. 21, 1990).

Wang et al., "Expression Cloning and Characterization of the TGF–β Type III Receptor" *Cell* 67(4):797–805 (Nov. 15, 1991).

Warren et al., "Elevated maternal plasma corticotropin–releasing hormone levels in pregnancies complicated by preterm labor" *Am. J. Obstet. Gynecol.* 166(4):1198–1207 (Apr. 1992).

Wongprasartsuk et al., "Inhibin and follistatin concentrations in fetal tissues and fluids during gestation in sheep: evidence for activin in amniotic fluid" *Journ. of Endocrinol.* 141:219–229 (1994).

Woodruff et al., "Rat Inhibin: Molecular Cloning of α and β–Subunit Complementary Deoxyribonucleic Acids and Expression in the Ovary" *Molecular Endocrinology* 1(8):561–568 (1987).

Wrana et al., "Two Distinct Transmembrane Serine/Threonine Kinases from Drosophila melanogaster Form an Activin Receptor Complex"*Molec. and Cell. Biology* 14(2):944–950 (Feb. 1994).

Ying et al., "Inhibin and Beta Type Transforming Growth Factor (TGFβ) Have Opposite Modulating Effects on the Follicle Stimulating Hormone (FSH)–Induced Aromatase Activity of Cultured Rat Granulosa Cells" *Biochemical and Biophysical Res. Comm.* 136(3):969–975 (May 14, 1986).

Ying et al., "Type Beta Transforming Growth Factor (TGF–β) Is A Potent Stimulator of the Basal Secretion of Follicle Stimulating Hormone (FSH) In A Pituitary Monolayer System" *Biochem. and Biophys. Res. Comm.* 135(3):950–956 (Mar. 28, 1986).

Ying, Shao–Yao, "Inhibins, Activins, and Follistatins: Gonadal Proteins Modulating the Secretion of Follicle–Stimulating Hormone"*Endocrine Reviews* 9(2):267–293 (1988).

Yohkaichiya et al, "Concentration of Immunoactive Inhibin in Serum During Human Pregnancy: Evidence for an Ovarian Contribution" *Reprod. Fertil. Dev.* 3:671–678 (1991).

Youngblood et al., "The Structural Genes Encoding P450scc and P450arom Are Closely Linked on Mlouse Chromosome 9" *Endocrinology* 125(5):2784–2789 (1989).

Yu et al., "Importance of FSH–releasing protein and inhibin in erythrodifferentiation" *Nature* 330(24):765–767 (Dec. 31, 1987).

Zhiwen et al., "Transforming growth factor β enhances basal and FSH–stimulated inhibin production by rat granulosa cells in vitro"*Molecular and Cellular Endocrinology* 58:161–166 (1988).

METHOD FOR PREDICTING AND/OR PREVENTING PRETERM LABOR

BACKGROUND OF THE INVENTION

1. Field of the Invention

This invention relates to methods to forecast premature labor in a pregnant mammal and to prolong the term of pregnancy thereof to avoid preterm delivery.

2. Description of Related and Background Art

Inhibin and activin are members of a family of growth and differentiation factors. The prototype of this family is transforming growth factor-beta (TGF-$\beta$). Derynck et al., *Nature*, 316: 701–705 (1985); Ying et al., *Biochem. Biophys. Res. Commun.*, 135: 950–956 (1986). Other members of the TGF-$\beta$ family include the Mullerian inhibitory substance, the fly decapentaplegic gene complex, and the product of Xenopus Vg-1 mRNA.

Inhibin is a glycoprotein produced by diverse tissues, including the gonads, pituitary, brain, bone marrow, placenta, and adrenal gland. It was initially identified by its ability to inhibit the secretion of follicle stimulating hormone (FSH) by the pituitary. De Jong and Sharpe, *Nature*, 263: 71–72 (1976); Schwartz and Channing, *Proc. Natl. Acad. Sci. USA*, 74: 5721–5724 (1977). Such preferential regulation of the gonadotropin secretion has generated a great deal of interest and prompted many laboratories in the past fifty years to attempt to isolate and characterize this substance from extracts of testis, spermatozoa, rete testis fluid, seminal plasma, and ovarian follicular fluid using various bioassays. Rivier et al., *Biochem. Biophys. Res. Commun.*, 133: 120 (1985); Ling et al., *Proc. Natl. Acad. Sci. USA*, 82: 7217 (1985); Fukuda et al., *Mol. Cell Endocrinol.*, 44: 55 (1985). The structure of inhibin, characterized from several species, consists of two disulfide-linked subunits: an $\alpha$ and either a $\beta_A$ or a $\beta_B$ chain.

After the identification of inhibin, activin was shown to exist in follicular fluid as a naturally occurring substance. Activin was found to be capable of stimulating FSH release by rat anterior pituitary cells. Vale et al., *Nature*, 321: 776–779 (1986); Ling et al., *Nature*, 321: 779–782 (1986); DePaolo et al., *Proc. Soc. Exp. Biol. Med.*, 198: 500–512 (1991); Ying, *Endocrine Rev.*, 9: 267–293 (1988). Recombinant activin was also found to stimulate pituitary LH and FSH in the adult male macaque. McLachlan et al., *Endocrinol.*, 125: 2787–2789 (1989). Activin consists of a homodimer or heterodimer of inhibin $\beta$ subunits, which may be $\beta_A$ or $\beta_B$ subunits. Vale et al., *Recent Prog. Horm. Res.*, 44: 1–34 (1988). There is 95–100% amino acid conservation of $\beta$ subunits among human, porcine, bovine, and rat activins including the prepro region. The $\beta_A$ and $\beta_B$ subunits within a given species are about 64–70% homologous.

The inhibin heterodimers $\alpha\beta_A$ and $\alpha\beta_B$ ("Inhibin A" and "Inhibin B," respectively) and the activin $\beta_A$ and $\beta_B$ homodimers and activin $\beta_A\beta_B$ heterodimer ("Activin A," "Activin B," and "Activin AB," respectively) have been identified in and purified from follicular fluid, and all these molecules have been cloned and their genes expressed. Mason et al., *Biochem. Biophys. Res. Commun.*, 135: 957 (1986); U.S. Pat. No. 4,798,885 issued Jan. 17, 1989; Mason et al., *Molecular Endocrinol.*, 3: 1352–1358 (1989); Schwall et al., *Mol. Endocrinol.*, 2: 1237–1242 (1988); Nakamura et al., *J. Biol. Chem.*, 267: 16385–16389 (1992). The complete sequence of the $\beta_B$ subunit is published in Serono Symposium Publications, entitled "Inhibin- Non-Steroidal Regulation of Follicle Stimulating Hormone Secretion," eds. Burger et al., abstract by Mason et al., vol. 42, pp. 77–88 (Raven Press, 1987), entitled "Human Inhibin and Activin: Structure and Recombinant Expression in Mammalian Cells." A method for purifying activin B is disclosed in U.S. Pat. No. 5,071,834. The recombinant activin molecule has been shown to increase serum levels of FSH in rats when delivered by subcutaneous injection. Schwall et al., *Endocrinol.*, 125: 1420–1423 (1989); Rivier and Vale, *Endocrinol.*, 129: 2463–2465 (1991).

Activin and inhibin regulate the growth and functions of a variety of cell types. They may be involved in diverse biological processes including erythropoiesis, bone formation, placental and gonadal steroidogenesis, neuronal survival, regulation of follicular matter, and embryologic mesodermal induction. In addition, activin has an effect on follicular granulosa cell differentiation (Sugino et al., *Biochem. Biophys. Res. Commun.*, 153: 281–288 [1988]), spermatogonial proliferation (Mather et al., *Endocrinol.*, 127: 3206–3214 [1990]), erythroid differentiation (EP 210,461 published Feb. 4, 1987 [where the protein is called BUF-3]; Eto et al., *Biochem. Biophys. Res. Commun.*, 142: 1095–1103 [1987] and Murata et al., *Proc. Natl. Acad. Sci. USA*, 85: 2434–2438 [1988] [where the activin is called EDF]; Yu et al., *Nature*, 330: 765–767 [1987] [where the activin is called FRP]), stimulation of insulin secretion by pancreatic islets (Totsuka et al., *Biochem. Biophys. Res. Commun.*, 156: 335–339 [1988]), enhancement of proliferation of fibroblast (Hedger et al., *Mol. Cell Endocrinol.*, 61: 133–138 [1989]), stimulation of glucose production by hepatocytes (Mine et al., *Endocrinology*, 125: 586–591 [1989]), induction of a dose-dependent increase in inositol phosphates in rat parenchymal liver cells, an effect also seen with EGF (Mine et al., *Biochem. Biophys. Res. Comm.*, 186: 205–210 [1992]), modulation of somatotroph functions (Billestrup et al., *Mol. Endocrinol.*, 4: 356–362 [1990]), modulation of nerve cell differentiation (Schubert et al., *Nature*, 344: 868–870 [1990]; Hashimoto et al., *Biochem. Biophys. Res. Comm.*, 173: 193–200 [1990]), and mesoderm induction. Smith et al., *Nature*, 345: 729–731 (1990); Mitrani et al., *Cell*, 63: 495–501 (1990).

The expression of inhibin subunits, each encoded by a separate gene, was demonstrated in several tissues in addition to ovary. Woodruff et al., *Molec. Endocrinol.*, 1: 561–568 (1987). Inhibin $\alpha$, $\beta_A$, and $\beta_B$ mRNAs were detected in testis, placental, spleen, pituitary, adrenal, bone marrow, and brain tissues. Meunier et al., *Proc. Natl. Acad. Sci. USA*, 85: 247–251 (1988). The expression of the inhibin subunit mRNAs varied by several-fold in a tissue-specific manner, suggesting different functions for these proteins depending on their pattern of association and their site of production. Activin mRNA ($\beta_A$ and $\beta_B$ subunits), bioactivity, and immunoactivity have been reported to be produced by testicular Leydig cells from immature rat and pig. Lee et al., *Science*, 243: 396–398 (1989); Lee et al., in Serono Symposium Publications, entitled "The Molecular and Cellular Endocrinology of the Testis" eds. Cooke and Sharpe, Vol. 50 (Raven Press: New York, 1988), p. 21–27.

Studies have shown that activin plays a role in embryo growth and differentiation. Mitrani et al., *Cell*, 63: 495–501 (1990); Roberts et al., *Endocrinology*, 128: 3122–3128 (1991); Smith et al., *Nature*, 345: 729–732 (1990); Thomsen et al., *Cell*, 63: 485–492 (1990); Van den Eijnden et al., *Nature*, 345: 732–734 (1990). Moreover, activin is synthesized by human trophoblast, maternal decidua, and fetal membranes (amnion and chorion) playing endocrine and paracrine roles in pregnancy. Petraglia et al., *Science*, 237: 187–189 (1987); Petraglia et al., *J. Endocrinol. Metab.*, 71:

487–492 (1990); Petraglia et al., *Am. J. Obstet. Gynecol.*, 165: 750–758; (1991); Rabinovici et al., *J. Clin. Endocrinol. Metab.*, 75: 571–576 (1992); Petraglia et al., *J. Clin. Endocrinol. Metab.*, 77: 542–548 (1993); Petraglia et al., *J. Clin. Endocrinol. Metab.*, 74: 1184–1188 [1992]; Minami et al., *Obstet. Gynecol.*, 80: 410–414 (1992); Petraglia et al., *Proc. Natl. Acad. Sci. USA*, 86: 5114–5117 [1989]; Manova et al., *Mech. Dev.*, 36: 141–152 (1992); and Tanimoto et al., *Biophys. Biochem. Res. Commun.*, 182: 773–778 (1992).

Activin beta A and B subunit mRNAs are expressed in human placental and decidual cells and mRNA levels increase throughout gestation, with highest values at term. Petraglia et al., *J. Endocrinol. Metab.*, 71 supra; Petraglia et al., *Am. J. Obstet. Gynecol.* (1991), supra. Also, activin A is present in maternal circulation and levels increase throughout pregnancy, and activin A serum levels decline immediately following delivery, becoming undetectable within 6 hours postpartum. Petraglia, *Endocr. J.*, 1: 323–327 (1993). Addition of human recombinant activin A increases the release of progesterone, GnRH, and hCG from cultured human placental cells [Petraglia et al., *Proc. Natl. Acad. Sci. USA*, 86: 5114–5117 (1989)] and of prostaglandin from cultured amnion cells [Petraglia et al., *J. Clin. Endocrinol. Metab.*, 77, supra] and increases endothelin secretion by the placenta. Brown et al., *Endocrinol.*, 129: 2355–2360 [1991].

In fact, an intense fluorescence signal for total immunoreactive inhibin/activin subunits and mRNAs have been identified in the epithelial layer of the amnion and chorion at term. Petraglia et al., *J. Clin. Endo. Metab.*, 77, supra. See also Petraglia et al., *J. Endocrinol. Invest.*, 16: 201–205 (1993) and Petraglia et al., *Int. J. Gynecol. Obstet.*, 404 (abstract) (1991). For reviews on the subject, see Baird and Smith, *Oxf. Rev. Reprod. Biol.*, 15: 191–232 (1993); Filicori, *Curr. Opin. Obstet. Gynecol.*, 3: 309–315 (1991); deKretser et al., *J. Endocrinol. Invest.*, 13: 611–624 (1990); deKretser et al., *J. Endocrinol.*, 117 (suppl.) Abs. 14 (1988); Petraglia, in *Hormone Gynecol. Endocrinol.*, ed. Genazzani et al. (Parthenon Publishers, Cornforth UK 1992), pp. 269–277.

It has been disclosed that there is an increased release of maternal activin A during parturition. Petraglia et al., *Obstet. Gynecol. Survey*, 48: 209–225 (1993); Norman et al., *Fert. Steril.*, 59: 130–137 (1993). See also McLean et al., *Obstet. Gynecol. Survey*, 48: 209–225 [1993]. By newly developed specific two-site enzyme-linked immunosorbent assay (ELISA), activin A has been measured in maternal circulation, cord blood, and amniotic fluid. Petraglia et al., *Obstet. Gynecol. Survey*, supra. Circulating maternal serum activin A concentration increases throughout gestation, and cord blood activin A was measurable at term. Petraglia et al., *Obstet. Gynecol. Survey*, supra. According to a possible role around parturition, the expression of the $\beta_A$ subunit is maximum at term. Petraglia et al., *J. Endocrinol. Metab.*, 71: 487–492 (1990). Activin A stimulates the release of prostaglandin E2 from amniotic cells, suggesting local paracrine/autocrine role. Petraglia et al., *J. Clin. Endocrinol. Metab.*, 77, supra. Further, oxytocin (Sawchenko et al., *Nature*, 334: 615–617 [1988]) and ACTH (Plotsky et al., *Endocrinol.*, 128: 2520–2525 [1991]) secretion is augmented in rats following activin administration and inhibited with β subunit antibodies. Studies performed on cultured placental cells have shown no changes in activin A secretion following the incubation with relaxin or forskolin. Rabinovici et al., supra.

In granulosa cells, activin has been reported to inhibit (and TGF-β to enhance) progesterone production. Ignotz and Massague, *J. Biol. Chem.*, 261: 4337 (1986). In primary cultures of granulosa cells, activin and inhibin as well as TGF-β were found to affect hormone synthesis and secretion, each in a different fashion. Adashi and Resnick, *Endocrinology*, 119: 1879 (1986); Ying et al., *Biochem. Biophys. Res. Commun.*, 136: 969 (1986); Hutchinson et al., *Biochem. Biophys. Res. Commun.*, 146: 1405 (1987); Mondschein et al., *Endocrinology*, 123: 1970 (1988); Feng et al., *J. Biol. Chem.*, 261: 14167 (1986). Inhibin α and $\beta_A$ subunit genes are expressed differentially in rat and mouse ovarian follicles during pregnancy. Penschow et al., *J. Mol. Endocrinol.*, 4: 247–255 (1990). These molecules have both positive and negative effects on FSH-dependent granulosa cell function. Carson et al., *J. Reprod. Fert.*, 85: 735–746 (1989). Also suggested is that individual members of the TGF-β/inhibin gene family regulate ovarian function, not only by direct action on follicle cells, but also indirectly by influencing the production rate of other members of that family. Zhiwen et al., *Molecular and Cellular Endocrinology*, 58: 161–166 (1988).

Activin and inhibin were reported to modulate growth of two gonadal cell lines, suggesting that these proteins may regulate proliferation as well as functions of gonadal cells. Gonzalez-Manchon and Vale, *Endocrinology*, 125: 1666–1672 (1989). It has now been shown that inhibin has a paracrine effect in stimulating ovarian follicular maturation [WO 91/10445] and that activin is useful for treating male infertility [U.S. Pat. No. 5,166,190], for treating polycystic ovarian disease when administered directly to the ovary [U.S. Pat. No. 5,102,868], for increasing the proportion of fertilized ova [U.S. Pat. No. 5,206,160], and for in vitro maturation of oocytes. PCT/US 94/02008.

Cell surface proteins that bind members of the TGF-β superfamily have been identified. See, e.g., WO 92/20793 and the references cited below. The nature of ligand binding and signaling is complicated and it is this intricacy that allows the cell to respond in a variety of different ways. Discrete receptors for inhibin A, inhibin B, and activin B have not been identified. The divergence evolutionarily of inhibin versus the TGF-β superfamily suggests that the receptor for this molecule may differ fundamentally from that of the activin binding moieties. Some of the identified orphan receptors may bind activin B.

The receptor subunits for the TGF-β superfamily were first identified based on crosslinking studies of iodinated activin or TGF-β to various cell types. A family of three binding moieties was identified using this methodology. The three membrane-derived binding moieties were named generically based on their molecular weight: Type I (55 kDa); Type II (70–85 kDa); and Type III (200–400 kDa).

The type III receptor was first identified as a beta-glycan present on the surface of most cells and having no signaling motif. See Wang et al., *Cell*, 67: 797–805 (1991). It is postulated that this cell surface binding protein binds TGF-β on the cell surface and makes this molecule readily available to the type I:type II receptor complex.

The type II receptor was identified by expression cloning based on binding iodinated ligand. The first type II receptor for activin A was identified and cloned by Mathews and Vale, *Cell*, 65: 973–982 (1991). Attisano et al. reported that the activin type II receptor was highly homologous to a second family of activin type II receptor isoforms named activin type $IIB_{1-4}$. Attisano et al., *Cell*, 68: 97–108 (1992). The unanticipated result of this research was that the type II receptors have a highly conserved serine-threonine kinase domain.

The type II receptors bind TGF-β or activin A with a variety of affinities which may contribute to the narrow concentration dependence of activin effects on different cell types. For example, the fate of the Xenopus blastomere greatly differs when exposed to different concentrations (1.5-fold differences) of activin A. The expression of activin type IIB receptors (ActRIIB) has been described in Xenopus embryo, rat placenta, and human placenta. Jaffe, in Yen and Jaffe, eds., *Reprod. Endocrinol.* (Philadelphia: W B Saunders, 1991), pp. 758–769; Peng et al., *Endocrinol.*, 133: 3046–3049 (1993). See also Roberts and Barth, *Endocrinol.*, 134: 914–923 (1994) on expression of mRNA encoding the inhibin/activin system during mid- and late-gestation rat embryogenesis. The localization of ActRIIB mRNA receptors in the external syncytial layer of placental villi corresponds to the cells producing hCG and progesterone (Petraglia, *Mol. and cell. Endocrin.*, 78: 109–112 [1991]), hormones whose secretion is modulated by activins. Petraglia et al., *Proc. Natl. Acad. Sci. USA*, 86: 5114–5117 (1989).

The type I receptor was identified by low-stringency PCR cloning based on the serine-threonine kinase domain. This strategy was the only method which could identify this component of the receptor complex because the type I receptor does not bind ligand in the absence of the type II subunit. Moreover, the signaling mechanism for activin/TGF-β requires the association of ligand with both subunits. See Attisano et al., *Cell*, 75: 671–680 (1993); ten Dijke et al., *Oncogene*, 8: 2879–2887 (1993); Matsuzaki et al., *J. Biol. Chem.*, 268: 12719–12723 (1993); Ebner et al., *Science*, 260: 1344–1348 (1993); and Wrana et al., *Molec. Cell. Biol.*, 14: 944–950 (1994).

Receptors for other members of the TGF-β superfamily have been identified based on PCR amplification of potential receptor members having similar serine-threonine kinase domains. A type I (daf-1) and type II (daf-4) receptor complex has been identified for BMP-2 and -4. Estevez et al., *Nature*, 365: 644–649 (1993). Lastly, four orphan human receptors have been identified which, based on their expression in mesenchymal cells adjacent to mullerian ducts during embryonic development, have been suggested to be MIS receptor isotypes. Matsuzaki et al., *J. Biol. Chem.*, 268: 12719–12723 (1993); ten Dijke et al., *Oncogene*, 8: 2879–2887 (1993).

A new class of gonadal protein factors, named follistatin or FSH-suppressing protein (FSP), was isolated from side fractions derived from purifying porcine and bovine ovarian inhibins and activins. Ying, *Endoc. Rev.*, 9: 267–293 (1988); Ling et al., "Isolation and characterization of gonadal polypeptides that regulate the secretion of follicle stimulating hormone," in Hodgen et al., eds., *Non-Steroidal Gonadal Factors: Physiological Roles and Possibilities in Contraceptive Development*, Jones Institute Press, Virginia, (1988), pp. 30–46. Follistatin was initially characterized by its ability to suppress FSH secretion from the pituitary. Thus, one biologic effect of follistatin is apparently similar to that of inhibin, but structurally the two proteins are quite different. Ueno et al., *Proc. Natl. Acad. Sci. USA*, 84: 8282–8286 (1987); Robertson et al., *Biochem. Biophys. Res. Commun.*, 149: 744–749 (1987).

Follistatin is a glycosylated single-chain protein that is found in forms having molecular weights ranging from 31 to 39 kDa. All of these forms have similar amino acid compositions and identical amino-terminal amino acid sequences. The molecular cloning of cDNA with the gene of follistatin revealed two forms, a smaller molecular weight form and a larger form, which are generated by alternative splicing. The smaller form represents a carboxy-terminal truncated form of the larger precursor. For a review on follistatin and activin, see DePaolo et al., supra. Follistatin is now thought to be an inhibin/activin binding protein. See also Tuuri et al., *J. Clin. Endo. Metab.*, 78: 1521–1524 (1994); Shi et al., *Endocrinol.*, 134: 2431–2437 (1994); deKretser et al., *Endocrinol.*, 134: 1231–1237 (1994); Petraglia et al., *J. Clin. Endo. Metab.*, 78: 205–210 (1994); Mercado et al., *Endocrinol.*, 132: 1774–1781 (1993); Torney et al., *J. Endocrinol.*, 133: 111–120 (1992); Spencer et al., *J. Clin. Endo. Metab.*, 71: 1678–1680 (1990); Kaiser et al., *Endocrinol.*, 126: 2768–2770 (1990); Wongprasartsuk et al., *J. Endocrinol.*, 141: 219–229 (1994).

Pregnant women with premature delivery have an increased risk of neonatal morbidity and death, showing a derangement of placental hormonal activity. Increased maternal concentration of relaxin, corticotropin-releasing factor, progesterone, or estrogen have been observed in association with preterm labor. McLean et al., supra; Norman et al., supra, Petersen et al., *J. Obstet. Gynecol.*, 99: 292–295 [1992]; Warren et al., *Am. J. Obstet. Gynecol.*, 166: 1198–1207 [1992]; Smith et al., *Gynecol. Obstet. Invest.*, 18: 252 [1984]. Most preterm labors remain unexplained and the rate of preterm delivery remains unchanged at about 5%. McLean et al., *Obstet. Gynecol. Survey*, 48: 209–225 (1993). Despite the widespread use of tocolytic drugs there has not been any documented decrease in the rate of preterm birth in the last two years. This is largely due to the fact that there is still a very limited understanding of the physiology of parturition and the causes of preterm labor. Iams, *J. Am. Med. Assoc.*, 262–265 (1989).

Since the development of a specific assay method, activin A is measurable in amniotic fluid and the highest concentrations have been found at labor. Petraglia et al., *Endo. J.*, 1: 323–327 (1993). See also Baly et al., *Endocrinol.*, 132: 2099–2108 (1993). Additionally, serum activin A levels increased significantly in pregnant women during vaginal or cesarean delivery after spontaneous labor. Petraglia et al., *Obstet. and Gynecol.*, 84: 278–282 (1994). Bioactive and total immunoreactive inhibin has also been detected in amniotic fluid of pregnant women at term. Yohkichiya et al., *Reprod. Fertil. Dev.*, 3: 671–678 (1991). All methods now available for measuring inhibin concentration recognize precursor molecules, mature forms of inhibin and free α subunit. Schneyer et al., *J. Clin. Endocrinol. Metab.*, 70: 1208–1212 (1990). Amniotic fluid is a compartment where biochemical markers have been investigated. Prostaglandins, tumor necrosis factor, interleukin-1, and interleukin-6 amniotic concentrations are higher in women with preterm labor. Qu and Thomas, *J. Clin. Endocrinol. Metab.*, 74: 1290–1295 (1992); Lopez et al., *Br. J. Obstet. Gynecol.*, 94: 1156–1158 (1987); Romero et al., *Am. J. Obstet. Gynecol.*, 166: 1576–1587 (1992); Romero et al., *Am. J. Obstet. Gynecol.*, 160: 1117–1123 (1989); Romero et al., *Am. J. Obstet. Gynecol.*, 169: 805–816 (1993). The introduction of a reliable prognostic biochemical marker would be of considerable value in women with preterm labor.

In addition, as noted above, there is clearly an unmet clinical need for preventing premature delivery of an infant.

Therefore, it is one object of the present invention to increase the length of a pregnancy so as to prolong delivery of an infant to avoid premature birth.

It is another object to provide a means for detecting whether premature labor is taking place by using activin A as a marker.

These and other objects will become apparent to one of ordinary skill in the art.

SUMMARY OF THE INVENTION

Accordingly, the present invention provides a method for avoiding premature labor in a pregnant mammal comprising administering to said mammal during labor, but before an infant is to be delivered, an effective amount of an activin antagonist.

In another aspect, this invention provides a method for assaying whether a pregnant mammal is in imminent delivery of its fetus in preterm labor comprising contacting a maternal serum sample or amniotic fluid sample of the mammal with a reagent that detects activin A and measuring the level of activin A in the serum or amniotic fluid.

In a further aspect, the invention provides a method for avoiding premature labor in a pregnant mammal comprising contacting a maternal serum sample or amniotic fluid sample of the mammal with a reagent that detects activin A; measuring the level of activin A in the serum or amniotic fluid; and if the measurement of activin A levels indicates that preterm labor is imminent or is occurring, administering to said mammal during labor, but before an infant is to be delivered, an effective amount of an activin antagonist to avoid premature labor in the mammal.

In a still further aspect, the invention provides a kit comprising a reagent that detects activin A and instructions or package insert or label for assaying whether a pregnant mammal is in imminent delivery of its fetus in preterm labor. The kit may further comprise a detection means and/or microtiter plates, an activin A standard or tracer, which is typically labeled, and an immobilized reagent that detects activin A, which is used to capture the activin A.

DESCRIPTION OF THE PREFERRED EMBODIMENTS

Figure 1:
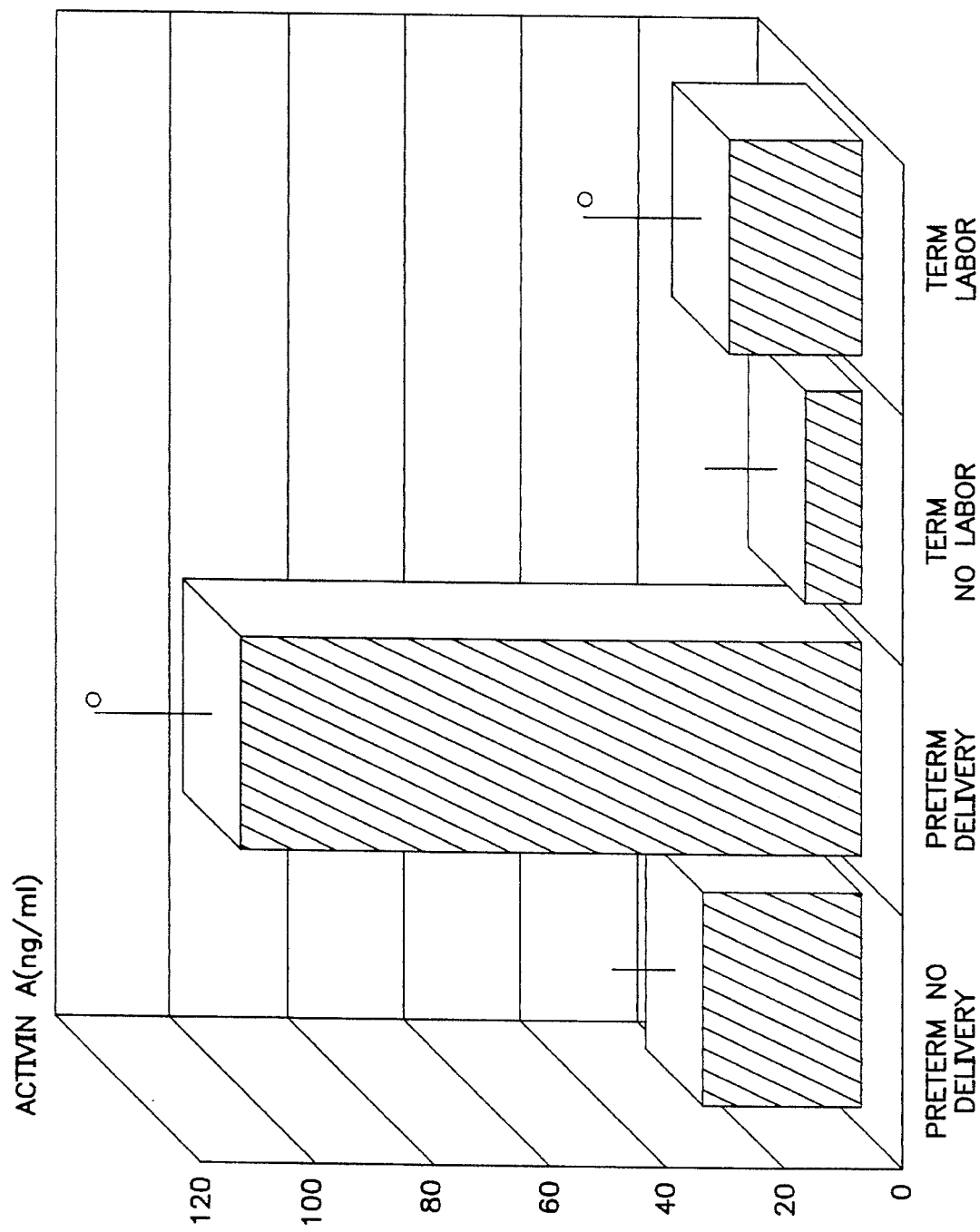
FIG. 1 shows the mean (±SDM) of maternal serum activin A concentration (ng/mL) in pregnant women with preterm labor who delivered within 48 hours from the diagnosis (n=30), in pregnant women who responded to the tocolytic treatment (n=8), in healthy pregnant controls in spontaneous labor (n=42), and in healthy pregnant patients at term (n=22). The circle indicates statistical significance.

Definitions:

As used herein, the expression "avoiding premature labor in a pregnant mammal" or "preventing preterm labor in a pregnant mammal" refers to allowing a pregnant mammal to carry the fetus beyond labor where the labor is occurring before the normal term for the pregnancy. For a human, premature labor is generally the onset of labor before the 37th completed week of pregnancy dated from the last normal menstrual period.

As used herein, "labor" refers to the process of expulsion of the fetus and the placenta from the uterus. The stages of labor are: first, the period of dilation of the os uteri; second, the stage of expulsive effort, beginning with the complete dilation of the cervix and ending with delivery of the infant; third, the period beginning with the delivery of the baby and ending with more or less complete expulsion of the placenta; and fourth, the period after the birth of the baby during which the membranes and placenta are extruded. The activin antagonist herein is given to the mammal during the first or second stage of labor but before the infant is being delivered or begins to proceed through the birth canal. Preferably, the activin antagonist is given during the period of dilation of the os uteri of the mammal.

As used herein, a pregnant mammal who is in "imminent delivery" generally refers to a mammal at the stage of pregnancy when delivery of the fetus will occur in no more than about 48 hours.

A "reagent that detects activin A" is a compound that is directly or indirectly labeled and is specific for activin A in that it binds in some fashion thereto or otherwise reacts with activin A to indicate its presence in maternal serum or amniotic fluid. Examples of such reagents include antibodies to activin A and follistatin.

For purposes herein, "activin antagonist" refers to any molecule that inhibits the activity of activin in causing premature labor. As used herein, "activin" refers to homo- or heterodimers of $\beta$ chains of inhibin, prepro forms, and pro forms, together with glycosylation variants thereof, whether in native form or synthetic or recombinant form. Activin A refers to activin with the two chains of $\beta_A$. Activin AB refers to activin with the chains $\beta_A$ and $\beta_B$. Activin B refers to activin with the two chains of $\beta_B$.

Typically the activin antagonist is a protein that binds to an active site of activin and includes, e.g., follistatin as described in Esch et al., *Mol. Endocrinol.*, 1: 849–855 [(1987); Shimasaki et al., *Proc. Natl. Acad. Sci. USA*, 85: 4218–4222 (1988); Shimasaki et al., *Biochem. Biophys. Res. Comm.*, 152: 717–723 (1988); Shimasaki et al., *Mol. Endocrinol.*, 3: 651–659 (1989); Ueno et al., *Proc. Natl. Acad. Sci. USA*, 84: 8282 (1987); Nakamura et al., *Science*, 247: 836 (1990); Shimonaka et al., *Endocrinology*, 128: 3313 (1991).

In addition, the antagonist may be a non-proteinaceous small molecule that acts as an activin antagonist. Such molecules can be screened by their ability to inhibit the action of activin in inducing premature labor using an assay such as that used for follistatin, as described, for example, in at least some of the above references, and for inhibin in some instances. Additionally, an assay can be used to identify molecules that inhibit RU486 from stimulating the onset of labor.

The definition of antagonist also includes an anti-activin antibody, whether polyclonal or monoclonal. The term "antibody" is used in the broadest sense and specifically covers single monoclonal antibodies, antibody compositions with polyepitopic specificity, as well as antibody fragments (e.g., Fab, F(ab')$_2$, and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature, 256: 495 (1975), or may be made by recombinant DNA methods (see, e.g., U.S. Pat. No. 4,816,567 [Cabilly et al.]). The "monoclonal antibodies" may also be isolated from phage antibody libraries using the techniques described in Clackson et al., Nature, 352: 624–628 (1991) and Marks et al., J. Mol. Biol., 222: 581–597 (1991), for example.

One example of preparing monoclonal antibodies specific for human recombinant activin A, AB, or B is the production as described by Corrigan et al., Endocrinology, 128: 1682 (1991). Briefly, inbred HPG-hypogonadal mice (Jackson Laboratories, Wilmington, Mass.) are hyperimmunized in the hind footpad with purified recombinant activin A, B, or AB. Cells harvested from the draining lymph nodes are then fused with the mouse myeloma line X63-Ag8.653. Kearney et al., J. Immunol., 123: 1548 (1979). The fusions are screened for reactivity and specificity in an ELISA using recombinant human activin A, activin B, activin AB, and inhibin A as coat proteins. Wong et al., Clinical Chemistry, 36: 192 (1990). Parental hybridomas that react specifically with either recombinant human activin A, B, or AB are cloned by limiting dilution. Ascites fluids are produced in Balb/c nu/nu mice, and antibody is purified by protein A-sepharose affinity chromatography (Repligen Corp., Cambridge, Mass.) according to established procedures (Goding, J. Immunol. Meth., 20: 241 [1978]; Ey et al., Immunochemistry, 15: 429 [1978]), and stored under sterile conditions in phosphate buffered saline (PBS) at 4° C.

Antibodies against activin or activin peptides that may also be suitable herein, although they may also cross-react with inhibin to some degree, include those described by Lofgren et al., J. Immunoassay, 12: 565 (1991); Shintani et al., J. Immunol. Meth., 137: 267 (1991); Groome and Lawrence, Hybridoma, 10: 309 (1991); Groome, J. Immunol. Meth., 145: 65–69 (1992); and Schwall et al., Non-Radiometric Assays: Technology and Application in Polypeptide and Steroid Hormone Detection, pp. 205–220 (Alan R. Liss, Inc., 1988).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., Proc. Natl. Acad. Sci. USA, 81: 6851–6855 [1984]).

"Humanized" forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al., Nature, 321: 522–525 (1986); Reichmann et al., Nature, 332: 323–329 (1988); and Presta, Curr. Op. Struct. Biol., 2: 593–596 (1992).

Another suitable activin antagonist herein is an inhibitor of activin such as that described in Shiozaki et al., Biochem. Biophys. Res. Commun., 183: 273–279 (1992), or a soluble form of an activin receptor.

Examples of suitable activin receptors include that described in U.S. Pat. No. 5,216,126, the disclosure of which is incorporated by reference. Briefly, the receptor is described as not binding to TGF-$\beta$, having a molecular weight on reduced 10% SDS-PAGE of 135–150 Kd, and having an N-terminal sequence beginning with ValLeuThr. To the extent that the "activin receptor" described in Mathews and Vale, Cell, 65: 1–20 [1991] and Mathews et al., Science, 255: 1702–1705 (1992), as well as WO 92/20793, blocks activin biological activity in hepatocytes, it is included herein. Activin receptors have also been reported by Attisano et al., Cell, 68: 97–108 [1992] and Kondo et al., Biochem. Biophys. Res. Comm., 181: 684–690 [1991].

The definition of activin antagonists also includes fragments of the above molecules that contain the active site needed to block activin activity, including F(ab) and Fc fragments of antibodies, etc.

Modes for Carrying Out the Invention:

The present invention concerns itself with using an activin antagonist to avoid or prevent premature or preterm labor in a pregnant mammal, including sports, zoo, pet, and farm animals such as dogs, cats, cattle, pigs, horses, monkeys, and sheep, endangered species, and humans. In another aspect, the invention provides a diagnostic tool for preterm labor and/or imminent delivery of a fetus.

In the first aspect, the method of this invention involves administering an activin antagonist to the mammal in an effective amount to avoid premature delivery of an infant.

Typically, the activin antagonist used in the method of this invention is formulated by mixing it at ambient temperature at the appropriate pH, and at the desired degree of purity, with pharmaceutically acceptable carriers, i.e., carriers that are non-toxic to recipients at the dosages and concentrations employed. Suitable carriers and their formulations are described in Remington's Pharmaceutical Sciences, 16th ed., 1980, Mack Publishing Co., edited by Oslo et al. These compositions will typically contain an effective amount of the activin antagonist, for example, from on the order of about 0.5 to about 10 mg/mL, together with a suitable amount of carrier to prepare pharmaceutically acceptable compositions suitable for effective administration to the patient.

The pH of the formulation depends mainly on the particular type and the concentration of antagonist, but preferably ranges anywhere from about 3 to about 8. Formulation in an acetate buffer at pH 5 is a suitable embodiment.

Compositions particularly well suited for the clinical administration of activin antagonist include sterile aqueous solutions or sterile hydratable powders such as lyophilized protein. Typically, an appropriate amount of a pharmaceutically acceptable salt is also used in the formulation to render the formulation isotonic.

Sterility is readily accomplished by sterile filtration through (0.2 micron) membranes. Activin antagonist ordinarily will be stored as an aqueous solution, although lyophilized formulations for reconstitution are acceptable.

The composition of activin antagonist will be formulated, dosed, and administered in a fashion consistent with good medical practice. Factors for consideration in this context include the particular mammal being treated, the clinical condition of the individual patient, the amount of activin in the general circulation (in the serum), the site of delivery of the agent, the method of administration, the scheduling of administration, and other factors known to medical practitioners. The "therapeutically effective amount" of activin antagonist to be administered will be governed by such considerations, and is the minimum amount necessary to prevent premature delivery of an infant. Such amount is preferably below the amount that is toxic to the mammal or renders the mammal significantly more susceptible to infections.

As a general proposition, the pharmaceutically effective amount of the activin antagonist administered parenterally per dose will be in the range of about 0.01 to 100 mg/kg of patient body weight per day, with the typical range of activin antagonist used being about 0.1 to 50 mg/kg/day. Interspecies scaling of dosages can be performed in a manner known in the art, e.g., as disclosed in Mordenti et al., *Pharmaceut. Res.*, 8: 1351 (1991) and in the references cited therein.

As noted above, however, these suggested amounts of activin antagonist are subject to a great deal of therapeutic discretion. The key factor in selecting an appropriate dose and scheduling is the result obtained, as indicated above.

The activin antagonist is administered to a subject mammal by any suitable means, including parenteral, subcutaneous, and intranasal administration. Examples of parenteral administration routes include intravenous, intrapulmonary, intraarterial, intramuscular, and intraperitoneal administration. Administration may be continuous or bolus dosing in sufficient amounts to maintain therapeutically effective levels. In addition, the activin antagonist is suitably administered by pulse infusion. Preferably the dosing is given by injections, most preferably intravenous or subcutaneous injections.

The activin antagonist need not be, but is optionally, combined or formulated with one or more therapies currently used to prevent premature labor. Examples of these therapies include tocolytic agents such as beta-receptor agonists, which have been shown by in vitro and in vivo pharmacologic studies in animals to exert a preferential effect on the $\beta_2$ adrenergic receptors such as those in the uterine smooth muscle. Stimulation of the $\beta_2$ receptors inhibits contractility of the uterine smooth muscle. Examples of such agonists include ritodrine hydrochloride, which is available under the brand name YUTOPAR® (tablets or formulated for injection) from Astra Pharmaceutical Products, Inc. (Westboro, Mass.) and available from Miolene, Lusofarmaco, Milan, Italy. Ritodrine hydrochloride is suitably administered intravenously according to the protocol described by Caritis et al., *Am. J. Obstet. Gynecol.*, 158: 380–384 [1988] and by the *Physicians Desk Reference*, 47th edition (1993).

The effective amount of such other agents depends mainly on the amount and type of activin antagonist present in the formulation, the mode, scheduling, and regimen for administering the agents, and other factors discussed above. These are generally used in the same dosages and with administration routes as used hereinbefore or about from 1 to 99% of the heretofore employed dosages. The activin antagonist and other agent may be formulated together in a single composition comprising therapeutically effective amounts of each of the agents in a pharmaceutical carrier having the appropriate pH for effective administration to the patient. Respective formulations of activin antagonist and other agent may be combined in vitro before administration or separately administered simultaneously, or in tandem, in either order, with any second administration taking place preferably within about 1–24 hours of the first administration, more preferably within about 1–5 hours.

If follistatin or antibodies are employed as the activin antagonist, they are prepared by any suitable technique, including those described above. Immunoglobulins (Ig) and certain variants thereof are known and many have been prepared in recombinant cell culture. For example, see U.S. Pat. No. 4,745,055; EP 256,654; EP 120,694; EP 125,023; EP 255,694; EP 266,663; WO 88/03559; Faulkner et al., *Nature*, 298: 286 (1982); Morrison, *J. Immun.*, 123: 793 (1979); Koehler et al., *Proc. Natl. Acad. Sci. USA*, 77: 2197 (1980); Raso et al., *Cancer Res.*, 41: 2073 (1981); Morrison et al., *Ann. Rev. Immunol.*, 2: 239 (1984); Morrison, *Science*, 229: 1202 (1985); and Morrison et al., *Proc. Natl. Acad. Sci. USA*, 81: 6851 (1984). Reassorted immunoglobulin chains are also known. See, for example, U.S. Pat. No. 4,444,878; WO 88/03565; and EP 68,763 and references cited therein. The immunoglobulin moiety may be obtained from IgG-1, IgG-2, IgG-3, or IgG-4 subtypes, IgA, IgE, IgD, or IgM, but preferably from IgG-1 or IgG-3.

Polyclonal antibodies to activin polypeptides or fragments are generally raised in animals by multiple subcutaneous (sc) or intraperitoneal (ip) injections of activin and an adjuvant. It may be useful to conjugate activin or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the activin or fragment, immunogenic conjugates, or derivatives by combining 1 mg or 1 µg of the peptide or conjugate (for rabbits or mice, respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for activin antibody titer. Animals are boosted until the titer plateaus. Preferably, the animal is boosted with the conjugate of the same activin, but conjugated to a different protein and/or through a different cross-linking reagent. Conjugates also can be made in recombinant cell culture as protein fusions. Also, aggregating agents such as alum are suitably used to enhance the immune response.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the activin monoclonal antibodies of the invention may be made using the hybridoma method first described by Kohler and Milstein, Nature, 256: 495 (1975), or may be made by recombinant DNA methods (Cabilly et al., supra).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59–103 [Academic Press, 1986]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, J. Immunol., 133: 3001 [1984]; Brodeur et al., Monoclonal Antibody Production Techniques and Applications, pp. 51–63 [Marcel Dekker, Inc., New York, 1987]).

Culture medium in which hybridoma cells are growing is assayed for production of monoclonal antibodies directed against activin. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson and Pollard, Anal. Biochem., 107: 220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA-encoding the antibody include Skerra et al., Curr. Opinion in Immunol., 5: 256–262 (1993) and Plückthun, Immunol. Revs., 130: 151–188 (1992).

In a further embodiment, antibodies or antibody fragments can be isolated from antibody phage libraries generated using the techniques described in McCafferty et al., Nature, 348: 552–554 (1990), using the activin to select for a suitable antibody or antibody fragment. Clackson et al., Nature, 352: 624–628 (1991) and Marks et al., J. Mol. Biol., 222: 581–597 (1991) describe the isolation of murine and human antibodies, respectively, using phage libraries. Subsequent publications describe the production of high affinity (nM range) human antibodies by chain shuffling (Mark et al., Bio/Technology, 10: 779–783 [1992]), as well as combinatorial infection and in vivo recombination as a strategy for constructing very large phage libraries (Waterhouse et al., Nuc. Acids. Res., 21: 2265–2266 [1993]). Thus, these techniques are viable alternatives to traditional monoclonal antibody hybridoma techniques for isolation of "monoclonal" antibodies which are encompassed by the present invention.

The DNA also may be modified, for example, by substituting the coding sequence for human heavy- and light-chain constant domains in place of the homologous murine sequences (Cabilly et al., supra; Morrison, et al., Proc. Nat. Acad. Sci., 81: 6851 [1984]), or by covalently joining to the immunoglobulin coding sequence all or part of the coding sequence for a non-immunoglobulin polypeptide.

Typically such non-immunoglobulin polypeptides are substituted for the constant domains of an antibody useful in the invention, or they are substituted for the variable domains of one antigen-combining site of an antibody of the invention to create a chimeric bivalent antibody comprising one antigen-combining site having specificity for one type of activin and another antigen-combining site having specificity for another type of activin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321: 522–525 [1986]; Riechmann et al., Nature, 332: 323–327 [1988];

Verhoeyen et al., *Science*, 239: 1534–1536 [1988]), by substituting rodent CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151: 2296 [1993]; Chothia and Lesk, *J. Mol. Biol.*, 196: 901 [1987]). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89: 4285 [1992]; Presta et al., *J. Immunol.*, 151: 2623 [1993]).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90: 2551–255 (1993); Jakobovits et al., *Nature*, 362: 255–258 (1993); Bruggermann et al., *Year in Immunol.*, 7: 33 (1993). Human antibodies can also be produced in phage-display libraries (Hoogenboom and Winter, *J. Mol. Biol.*, 227: 381 [1991]; Marks et al., *J. Mol. Biol.*, 222: 581 [1991]).

Another aspect of the invention is an assay to determine whether a pregnant mammal is in imminent delivery of its fetus in preterm labor. Once this is determined, the pregnant mammal can be administered the activin antagonist to act as a preventative agent to ward off any premature labor before it occurs. This method comprises contacting a serum sample or amniotic fluid sample of the mammal with a reagent that detects activin A and measuring the level of activin A in the serum or amniotic fluid.

In a preferred embodiment, the reagent is a labeled antibody that binds to activin A or is labeled follistatin, i.e., labeled with a detectable moiety. The detectable moiety can be any one which is capable of producing, either directly or indirectly, a detectable signal. Labels are further described below.

The maternal serum and amniotic fluid samples are taken from the mammal using any acceptable method, typically by syringe.

The step of contacting the samples with the detecting reagent may be accomplished by any suitable technique so that detection can occur. Suitable assay methods involving antibodies include, e.g., competitive binding assays, direct and indirect sandwich assays, and immunoprecipitation assays. Zola, *Monoclonal Antibodies: A Manual of Techniques*, pp. 147–158 (CRC Press, Inc., 1987). Other methods include radioimmunoassays (RIA) and radioreceptor assays (RRA), which are well known in the art.

In particular, competitive, sandwich and steric inhibition immunoassay techniques are useful. The competitive and sandwich methods employ a phase-separation step as an integral part of the method while steric inhibition assays are conducted in a single reaction mixture. The substance to be tested (activin A) is referred to herein as an analyte, and proteins that bind to the analyte are denominated binding partners, whether they be antibodies or cell-surface receptors.

Analytical methods for activin A all use one or more of the following reagents, which can be included in a kit: labeled analyte analogue, immobilized analyte analogue, labeled binding partner, immobilized binding partner, and steric conjugates. The labeled reagents also are known as "tracers."

The label used (and this is also useful to label activin A nucleic acid for use as a probe) is any detectable functionality that does not interfere with the binding of analyte and its binding partner. Numerous labels (or detectable moieties) are known for use in immunoassay, examples including moieties that may be detected directly, such as fluorochrome, chemiluminscent, and radioactive labels, as well as moieties, such as enzymes, that must be reacted or derivatized to be detected. Examples of such labels include a radioisotope, such as, e.g., $^{32}P$, $^{14}C$, $^{125}I$, $^{3}H$, $^{35}S$, and $^{131}I$; fluorophores (fluorescent or chemiluminescent compounds) such as rare earth chelates or fluorescein and its derivatives (e.g., fluorescein isothiocyanate); rhodamine and its derivatives; dansyl; umbelliferone; luciferases, e.g., firefly luciferase and bacterial luciferase (U.S. Pat. No. 4,737,456); luciferin; 2,3-dihydrophthalazinediones; enzymes such as malate dehydrogenase; urease; peroxidase such as horseradish peroxidase (HRP); alkaline phosphatase; β-galactosidase; glucoamylase; lysozyme; saccharide oxidases, e.g., glucose oxidase, galactose oxidase, and glucose-6-phosphate dehydrogenase; heterocyclic oxidases such as uricase and xanthine oxidase, coupled with an enzyme that employs hydrogen peroxide to oxidize a dye precursor such as HRP, lactoperoxidase, or microperoxidase; biotin/avidin; spin labels; bacteriophage labels; stable free radicals; and the like.

Those of ordinary skill in the art will know of other suitable labels that may be employed in accordance with the present invention. The binding of these labels to activin A or its antibodies or binding partners can be accomplished using standard techniques commonly known to those of ordinary skill in the art. For instance, coupling agents such as dialdehydes, carbodiimides, dimaleimides, bis-imidates, bis-diazotized benzidine, and the like may be used to tag the polypeptide with the above-described fluorescent, chemiluminescent, and enzyme labels. See, for example, U.S. Pat. Nos. 3,940,475 (fluorimetry) and 3,645,090 (enzymes); Hunter et al., *Nature,* 144: 945 (1962); David et al., *Biochemistry,* 13: 1014–1021 (1974); Pain et al., *J. Immunol. Methods,* 40: 219–230 (1981); Nygren, *J. Histochem. and Cytochem.,* 30: 407–412 (1982); O'Sullivan et al., "Methods for the Preparation of Enzyme-antibody Conjugates for Use in Enzyme Immunoassay," in *Methods in Enzymology,* ed. J. J. Langone and H. Van Vunakis, Vol. 73 (Academic Press, New York, N.Y., 1981), pp. 147–166; Kennedy et al., *Clin. Chim. Acta,* 70: 1–31 (1976); and Schurs et al., *Clin. Chim. Acta,* 81: 1–40 (1977). Coupling techniques mentioned in the lattermost reference are the glutaraldehyde method, the periodate method, the dimaleimide method, and the m-maleimidobenzyl-N-hydroxysuccinimide ester method.

In the practice of the present invention, enzyme labels are a preferred embodiment. No single enzyme is ideal for use as a label in every conceivable assay. Instead, one must determine which enzyme is suitable for a particular assay system. Criteria important for the choice of enzymes are turnover number of the pure enzyme (the number of substrate molecules converted to product per enzyme site per unit of time), purity of the enzyme preparation, sensitivity of detection of its product, ease and speed of detection of the enzyme reaction, absence of interfering factors or of enzyme-like activity in the test fluid, stability of the enzyme and its conjugate, availability and cost of the enzyme and its conjugate, and the like. Included among the enzymes used as preferred labels in the assays of the present invention are alkaline phosphatase, HRP, beta-galactosidase, urease, glucose oxidase, glucoamylase, malate dehydrogenase, and glucose-6-phosphate dehydrogenase. Urease is among the more preferred enzyme labels, particularly because of chromogenic pH indicators that make its activity readily visible to the naked eye.

Immobilization of reagents is required for certain assay methods. Immobilization entails separating the binding partner from any analyte that remains free in solution. This conventionally is accomplished by either insolubilizing the binding partner or analyte analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the partner or analogue afterward, e.g., by immunoprecipitation.

Other assay methods, known as competitive or sandwich assays, are well established and widely used in the commercial diagnostics industry.

Competitive binding assays rely on the ability of a labeled standard (which may be activin A or an immunologically reactive portion thereof), or tracer analogue, to compete with the test sample analyte (activin A) for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of activin A in the test sample is inversely proportional to the amount of tracer (or standard) that becomes bound to the antibodies, as measured by the amount of marker substance. To facilitate determining the amount of standard that becomes bound, the antibodies generally are insolubilized before or after the competition, so that the standard and analyte that are bound to the antibodies may conveniently be separated from the standard and analyte which remain unbound. Dose-response curves with known amounts of analyte are prepared and compared with the test results to quantitatively determine the amount of analyte present in the test sample. These assays are called ELISA systems when enzymes are used as the detectable markers.

Another species of competitive assay, called a "homogeneous" assay, does not require a phase separation. Here, a conjugate of an enzyme with the analyte is prepared and used such that when anti-analyte binds to the analyte the presence of the anti-analyte modifies the enzyme activity. In this case, activin A is conjugated with a bifunctional organic bridge to an enzyme such as peroxidase. Conjugates are selected for use with anti-activin A so that binding of the anti-activin A inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate, resulting in a change in the character of the conjugate hapten, e.g., a change in fluorescence when the hapten is a fluorophore.

Sandwich assays particularly are useful for the determination of activin A. Sandwich assays involve the use of two antibodies; each capable of binding to a different immunogenic portion, or epitope, of the activin A to be detected. In a sandwich assay, the test sample analyte is bound by a first antibody which is immobilized on a solid support, and thereafter a second antibody binds to the analyte, thus forming an insoluble three-part complex. David and Greene, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme (e.g., horseradish peroxidase).

An example of a suitable ELISA is the one-step (simultaneous) monoclonal antibody based ELISA (2F8:6H5) as described by Krummen et al., *Endocrinology,* 132: 431–443 [1993] or by Romero et al., *Am. J. Obstet. Gynecol.,* 165: 821–830 (1991).

In sequential sandwich assays an immobilized binding partner is used to adsorb test sample analyte, the test sample is removed as by washing, the bound analyte is used to adsorb labeled binding partner, and bound material is then separated from residual tracer. The amount of bound tracer is directly proportional to test sample analyte. In "simultaneous" sandwich assays the test sample is not separated before adding the labeled binding partner. A sequential sandwich assay using an anti-activin A monoclonal antibody as one antibody and a polyclonal anti-activin A antibody as the other is useful in testing samples for activin A activity.

The foregoing are merely exemplary diagnostic assays for activin A. Other methods now or hereafter developed for the determination of activin A are included within the scope hereof.

The invention will be more fully understood by reference to the following examples. They should not, however, be construed as limiting the scope of the invention. All literature and patent citations are expressly incorporated by reference.

EXAMPLE I

Study Design

A cross-sectional study was conducted in four groups of pregnant women:
group 1) with preterm labor (n=38) (gestational age between 25 and 35 weeks);
group 2) healthy controls (n=21) (gestational age between 27 and 37 weeks);
group 3) healthy at term not in labor (n=22) (gestational age between 38 and 40 weeks);
group 4) healthy at term in spontaneous labor (n=42) (labor stage 1: cervical dilatation<3 cm) (gestational age between 39 and 41 weeks).

Informed consent was obtained from all patients. The Local Ethical Committee approved the study protocol. Preterm labor was defined as the presence of regular uterine contractions with a frequency of at least two every 10 minutes associated with changes in the cervical Bishop's score. Rupture of membranes was excluded by testing for pooling, nitrazine paper reaction, and ferning. Ritodrine hydrochloride (Miolene, Lusofarmaco, Milan, Italy) was administered intravenously as the tocolytic agent to all patients, according to the protocol described by Caritis et al., *Am. J. Obstet. Gynecol.*, 158: 380–384 [1988]. Failure of tocolysis was defined as progressive cervical dilatation to 5 cm or delivery. Among patients of group 1 a failure of tocolytic treatment was described in some of the 42 patients. All patients studied were hospitalized to assess the efficacy of previous diet, with two pregnant women treated by low-diet therapy. No fetal malformation was detected. Postnatal life was normal in all newborns. At delivery three infants were macrosomic (birth weight 4.500±sg).

In all patients and controls a single venous blood specimen (4–6 mL) was collected at the time of the admission, inserting into an arm vein a 18-gauge long-dwell catheter with a three-way stopcock. Blood was collected in ice-chilled polypropylene tubes and centrifuged at 1000×g for 15 minutes. Serum specimens were stored at −20° C. until assayed.

Cord Blood Sampling

Cord blood samples were collected (at term with no labor, at preterm labor, control 25–36 weeks) by cordonocentesis (performed for the diagnosis of fetal hypoxia). Cord blood (1–2 mL) was obtained by cannulating the cord with a 22-gauge needle guided by ultrasound. Blood was tested as for maternal specimens.

Activin A Assay

Activin A concentration was measured using a one-step (simultaneous) monoclonal antibody based ELISA (2F8:6H5) as described by Krummen et al., *Endocrinology*, 132: 431–443 [1993]. Briefly, Nunc Immunlon Maxisorp microtiter plates were coated overnight (2F8, 4 g/mL). Standard controls or diluted samples (1:5 or 1:10) and freshly diluted horseradish-peroxidase-conjugated 6H5 antibody were added in 20% normal human serum to each reagent/well and incubated for 2 hours at room temperature. The assay limit of detection was 200 pg/mL. The inter- and intra-assay coefficients of variation were 6.5% and 2.4%, respectively. Caritis et al., supra. The antiserum does not cross-react with recombinant human activin B, recombinant human inhibin A, recombinant human follistatin, or α2-macroglobulin.

Statistical Analysis

The statistical analysis of the results was performed using analysis of variance followed by the test of Duncan.

Results

Among patients, 18/38 with preterm labor showed single values of activin A concentration higher than those of healthy controls (M±SDM). Mean maternal serum activin A levels in pregnant women with preterm labor who delivered within 48 hours (n=30) were significantly higher than in patients who responded to tocolysis (n=8) and in normal pregnant women at term or in labor (P<0.01) (FIG. 1).

Figure 2:
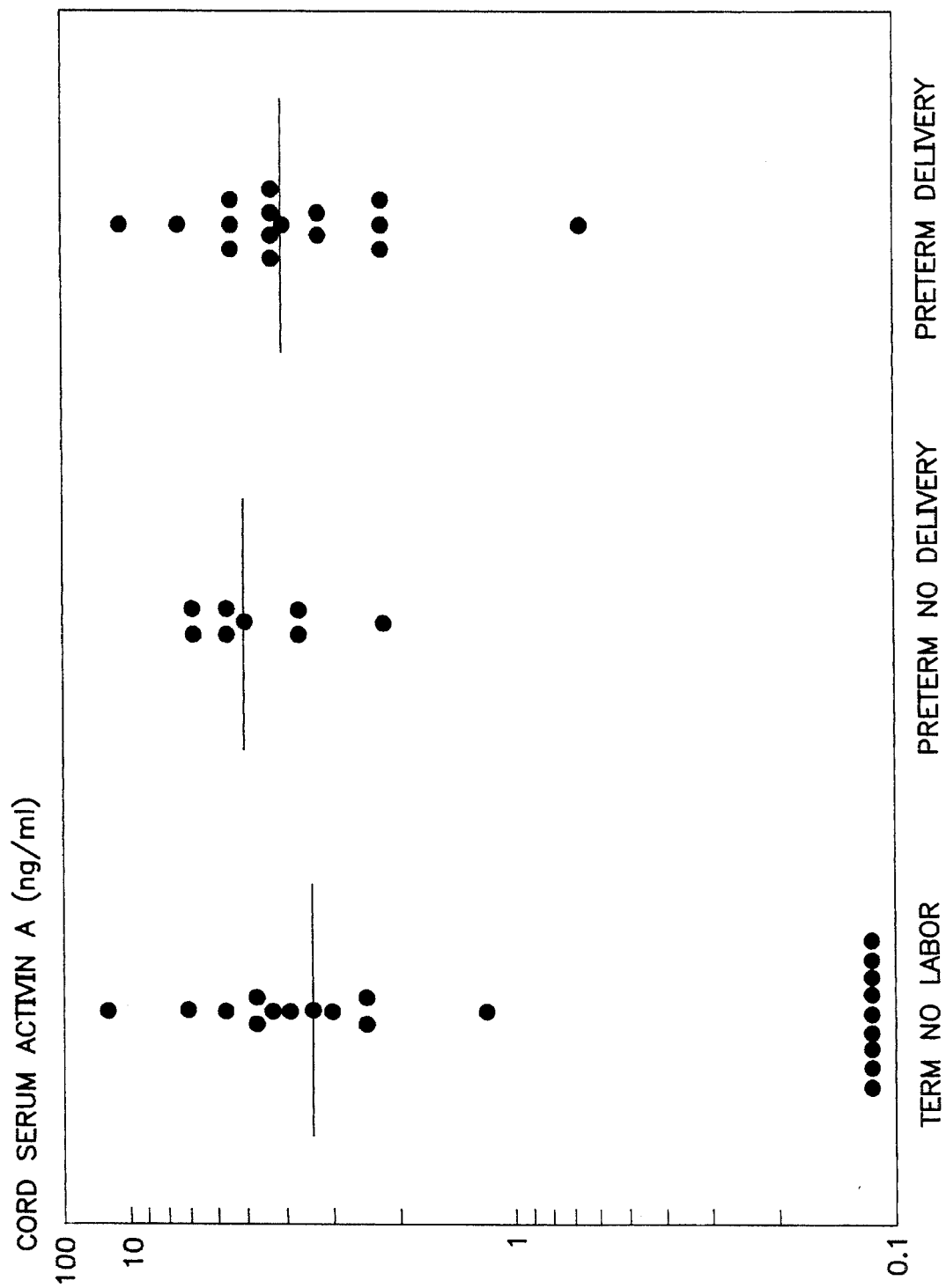
FIG. 2 shows cord serum activin A concentration (ng/mL) in pregnant women with preterm labor (with or without delivery) versus that in healthy controls at term.

Activin A concentration in cord blood serum of healthy women was measurable only in 2/16 specimens collected during pregnancy and was significantly lower than in maternal circulation (P<0.01). Cord serum activin A concentration in pregnant women with preterm labor was measurable in all specimens, and mean levels did not significantly differ from those of women at term. No significant difference was found between activin A concentration in women who delivered within 48 hours and those who responded to tocolytic treatment (FIG. 2).

This study shows that preterm labor is associated with a high concentration of activin A in maternal serum in a large number of patients. The highest values of maternal serum activin A concentration were found in pregnant women with preterm labor not responsive to tocolytic therapy, and who delivered within 48 hours. This indicates that activin concentration is a predictive signal of imminent delivery in preterm labor, and high levels indicate a predisposition or correlation with preterm labor. Maternal serum activin A concentration was significantly higher in women during labor than at term.

In contrast to healthy controls, activin A was measurable in the cord blood of patients with preterm labor, but the concentration did not correlate with the time of delivery. Thus, cord serum activin A levels in women with preterm labor were in the same range as that of women at term, and no significant difference between those who delivered and those who responded to tocolytic treatment was observed. Activin A concentration in maternal circulation at term was 2–10 fold higher than in cord blood.

EXAMPLE II

Experimental

A cross-sectional study was conducted in pregnant women at term and with preterm labor (gestational age between 23 and 36 weeks) and intact membranes. Informed consent was obtained from all patients. The Local Ethical Committee approved the study protocol. Preterm labor was defined as the presence of regular uterine contractions with a frequency of at least two every 10 minutes associated with changes in the cervical Bishop's score. Ritodrine was administered intravenously as the tocolytic agent to all patients, according to the protocol described by Caritis et al., supra. Amniocentesis was performed before the initiation of tocolytic therapy. Failure of tocolysis was defined as progressive cervical dilatation to 5 cm or delivery.

Pregnant women were subdivided into 7 groups:
1—healthy controls at term with no labor (n=25)
2—healthy controls at term with spontaneous labor (n=40)
3—healthy controls at term with .microbiological invasion of amniotic cavity (n=25)

4—patients with preterm labor who responded to tocolysis (n=19)

5—patients with preterm labor who delivered<48 hours (n=13)

6—patients with preterm labor with MIAC who responded to tocolysis (n=12)

7—patients with preterm labor with MIAC who delivered<48 hours (n=13).

Amniotic fluid was obtained by transvaginal amniocentomy from healthy pregnant women at term or preterm in labor (for microbiologic assessment of the amniotic cavity) and by amniocentesis in pregnant women at term and preterm not in labor (for the assessment of fetal lung maturity). Amniotic fluid specimens were collected in polypropylene tubes. After a centrifugation at 1000×g for 15 min., the clear supernatant was divided in aliquots and stored at −20° C. until assayed.

Amniotic fluid was sent immediately to the hospital's clinical laboratory for Gram stain, aerobic and anaerobic, and determination of L:S ratio, in a capped plastic syringe immediately after collection. These conditions preclude air contact with the specimen. Plating occurred within 30 minutes of collection in all cases. Patients with a positive Gram stain received parenteral antibiotics (generally gentamycin and ampicillin), and tocolysis was discontinued. Amniotic fluid (AF) was cultured for aerobic and anaerobic bacteria, as well as Mycoplasma species. Microbial invasion of the amniotic cavity was evidenced by a positive AF culture or a combination of positive Gram stain, positive Limulus Amebocyte lysate assay (to detect endotoxin), or AF white blood cell (WBC) count>50 cells/mm$^3$. Romero et al., *Am. J. Obstet. Gynecol.*, 165: 821–830 (1991). Mycoplasma were the most common microorganisms isolated from the amniotic cavity.

Activin A levels were measured using a one-step (simultaneous) monoclonal antibody based ELISA (2F8:6H5) as described by Romero et al., supra. Briefly, Nunc Immunlon Maxisorp microtiter plates were coated overnight (2F8, 4 g/mL). Standard controls or diluted samples (1:5 or 1:10) and freshly diluted horseradish-peroxidase-conjugated 6H5 antibody were added in 20% normal human serum to each reagent/well and incubated for 2 hours at room temperature. The assay limit of detection was 200 pg/mL. The inter- and intra-assay coefficients of variation were 6.5% and 2.4%, respectively. Caritis et al., supra. The antiserum does not cross-react with human recombinant activin B, human recombinant inhibin A, human recombinant follistatin, or α2-macroglobulin.

Total immunoreactive inhibin concentration was measured using a sensitive inhibin A ELISA. The ELISA uses a polyclonal chicken antibody (Ck) to purified human recombinant inhibin A for capture and biotinylated chicken anti-inhibin A for detection. Krummen et al., supra. In each format, 200 μl of coat antibody was added to 96-well microtiter plates (Immunol I, Nunc, Roskilde, Denmark) at 2 μg/mL. After overnight incubation at 4° C., plates were washed six times with ELISA wash buffer and blocked for one hour with ELISA diluent. After the plates were washed again six times with ELISA wash buffer, the antiserum was freshly diluted to its optimum concentration in ELISA diluent and was added to duplicate wells and incubated overnight at 4° C. The antiserum does not cross-react with recombinant human activin A or recombinant human activin B nor is it interfered with by α2-macroglobulin or recombinant human follistatin. The inter- and intra-assay variation was <10% and 5%, respectively. The assay detects inhibin A and inhibin B precursor forms, 32K inhibin A, 32K inhibin B, and free α-subunit. The immunoreactivity detected by this assay is called "total inhibin immunoreactivity." The statistical analysis of the results was done by using analysis of variance.

Results

Activin A and total immunoreactive inhibin were measurable in the amniotic fluid of all samples studied.

Figure 3:
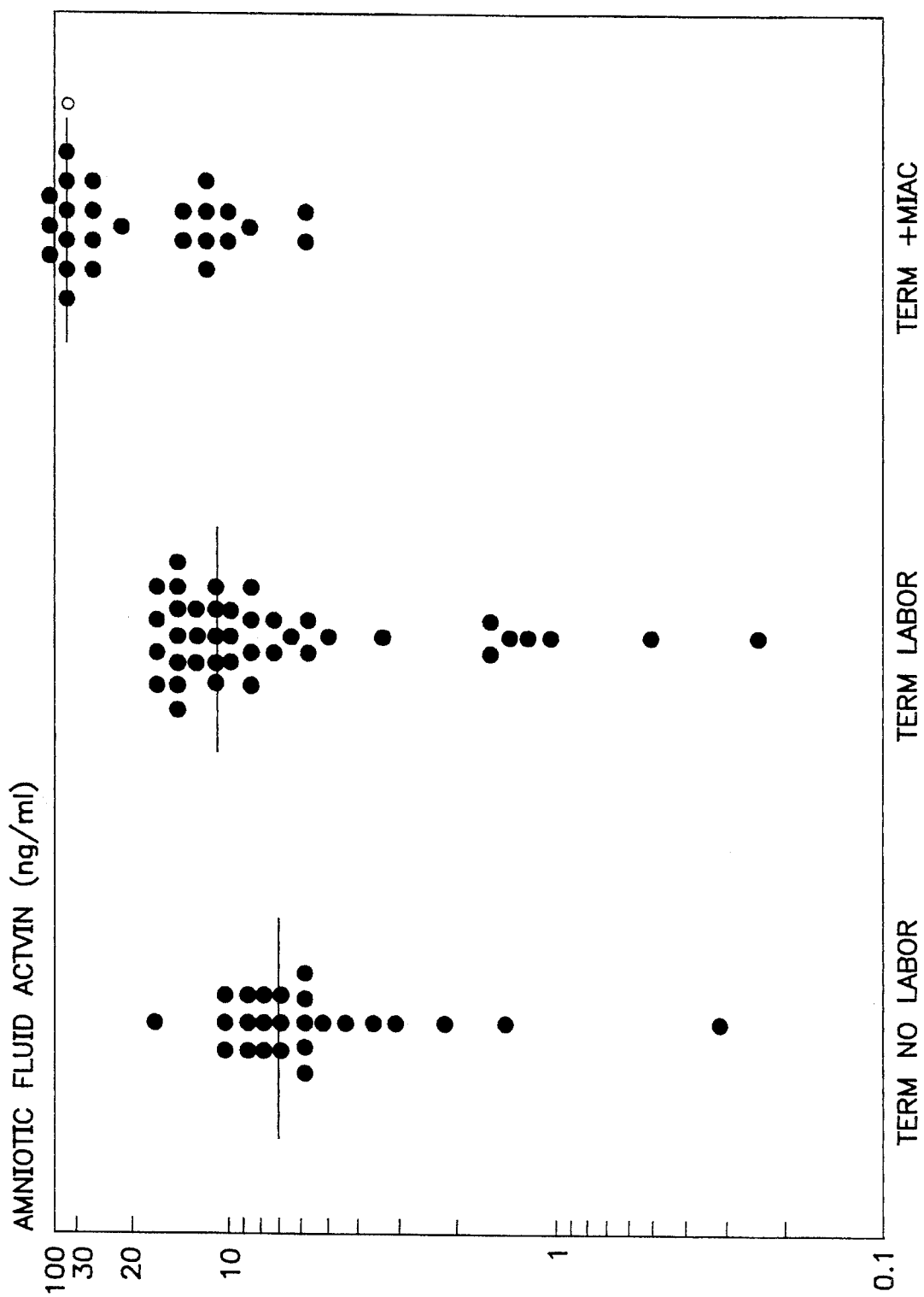
FIG. 3 shows amniotic fluid activin A concentration (ng/mL) in control pregnant women at term not in labor, at term in labor, and at term with microbial invasion of the amniotic cavity (MIAC). The line represents the mean value, and the open circles represent statistical significance.
Figure 4:
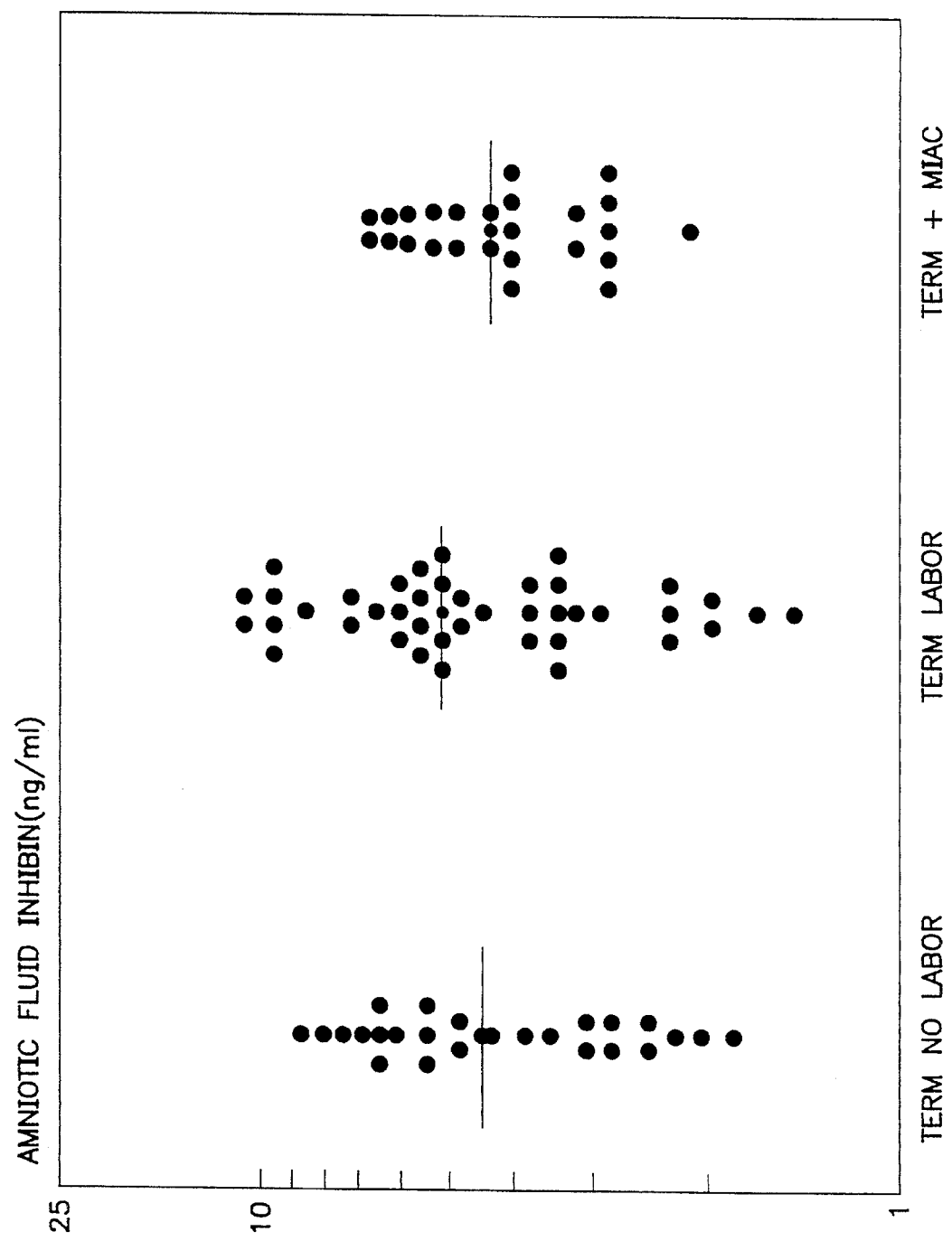
FIG. 4 shows amniotic fluid total immunoreactive inhibin concentration (ng/mL) in control pregnant women at term not in labor, at term in labor, and at term with MIAC. The line represents the mean value.

Mean (±SEM) amniotic fluid activin A concentration (10.51±0.88 ng/mL) in women at term in labor was significantly higher (P<0.001) than in controls not in labor (7.18±0.69 ng/mL), and the highest values were found in pregnant women at term with MIAC (34.72±5.63 ng/mL) (FIG. 3). No significant difference was observed for amniotic fluid total inhibin immunoreactivity in healthy women at term, during labor and with infection (FIG. 4).

Figure 5:
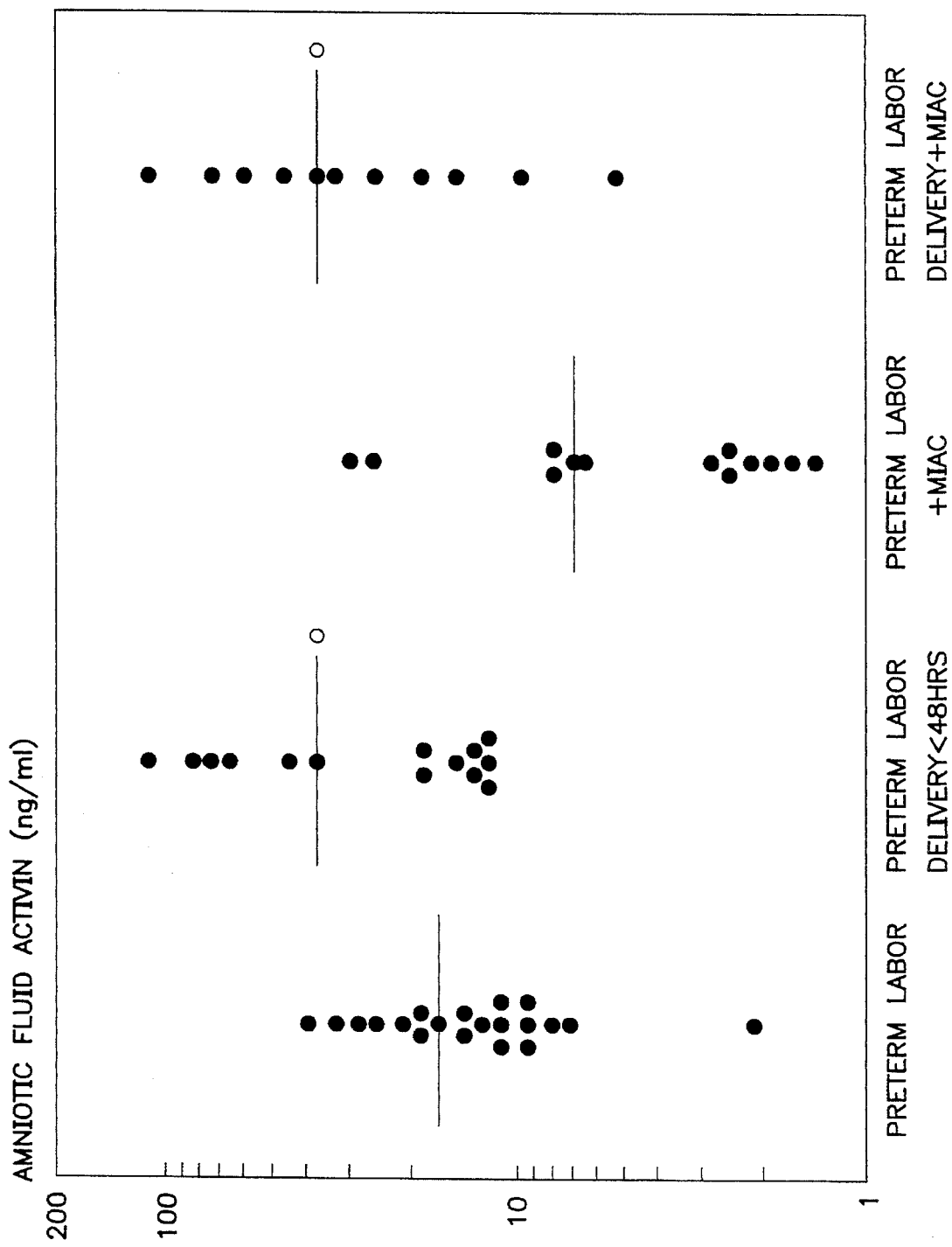
FIG. 5 shows the amniotic fluid activin A concentration (ng/mL) in pregnant women with preterm labor who delivered within 48 hours, with or without the MIAC, compared to that of those patients who responded to tocolysis (*P<0.01). The open circles represent statistical significance.
Figure 6:
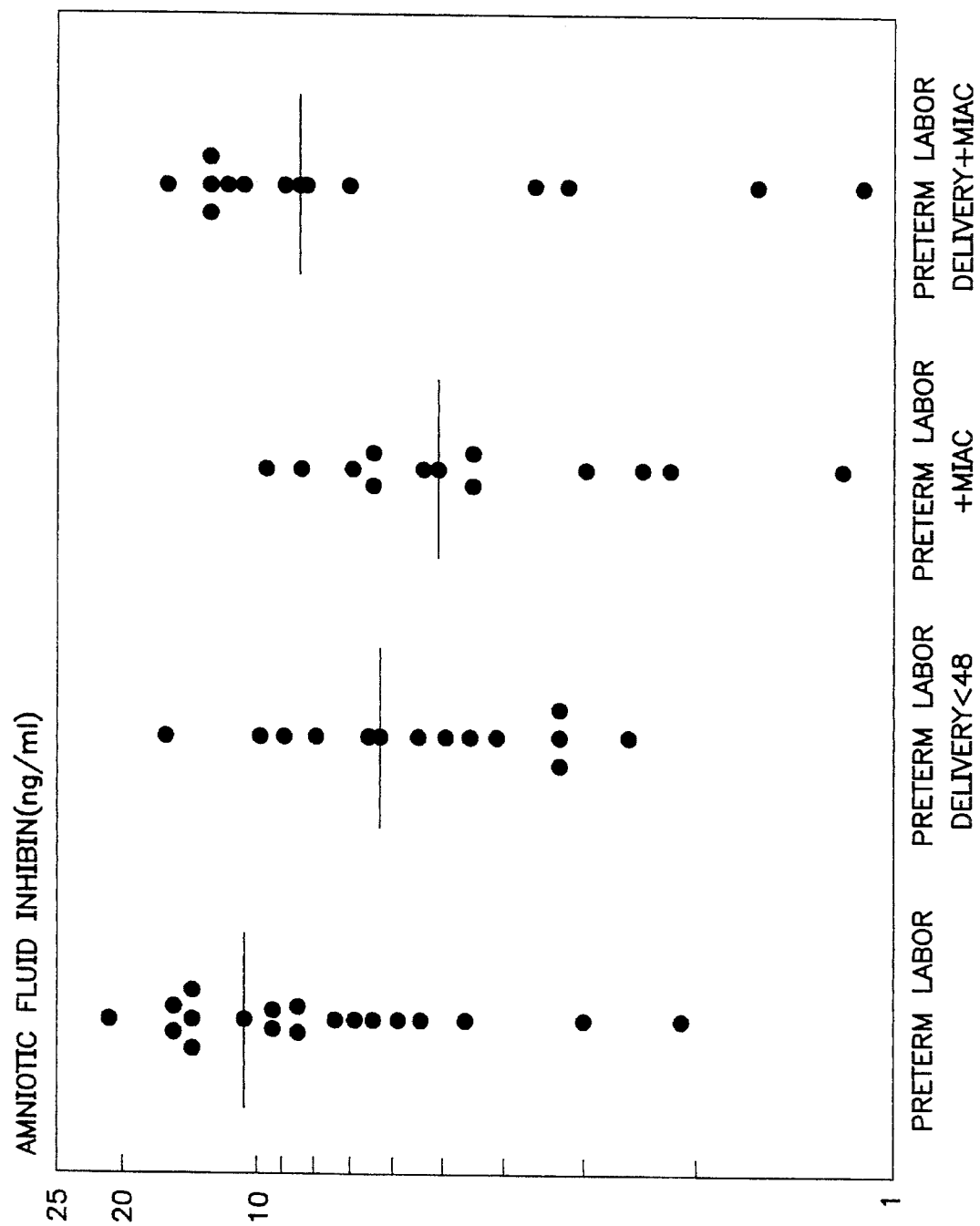
FIG. 6 shows amniotic fluid total immunoreactive inhibin concentration (ng/mL) in pregnant women with preterm labor who delivered within 48 hours, with or without the MIAC, compared to that of those patients who responded to tocolysis.

The group of pregnant women with preterm labor showed a concentration of amniotic fluid activin A significantly higher than that of controls at term (P<0.01). The highest concentration of activin A in amniotic fluid was found in pregnant women with preterm labor who delivered within 48 hours, with or without microbial invasion (FIG. 5). No significant differences were observed for amniotic fluid total inhibin immunoreactivity between the four groups of pregnant women with preterm labor (FIG. 6).

The present study shows that preterm labor is associated with high values of activin A concentration in amniotic fluid. The highest amniotic fluid activin A levels are correlated with imminent delivery (within 48 hours), while the microbial invasion of amniotic cavity does not influence amniotic fluid activin A levels.

Since no significant correlation was found between total immunoreactive inhibin and activin A concentration, this shows an independent secretion of these two hormones in the amniotic fluid. Activin A in amniotic fluid may be used as a prognostic factor in preterm delivery.

EXAMPLE III

Forty pregnant women (primigravidas and multiparas) between 19 and 37 years of age were studied after having given their informed consent. Permission of the local Human Investigation Committee was granted. All were healthy and normal pregnant women who met the following criteria for admission to the study: absence of any complication throughout gestation, normal fetal growth as determined by serial ultrasound assessments, absence of fetal distress as revealed by cardiotocographic monitoring, and a 1-minute Apgar score of 8–10 at birth for newborns delivered between the 38th and 40th weeks of gestation and weighing 3000–4150 g. Delivered placentas were normal, with a mean weight of 509 g (range 420–690 g). The newborn male-to-female sex ratio was 1 to 1.5.

The women were subdivided into three groups: group 1 included 15 primigravidas who were studied at vaginal delivery between the 39th and 40th weeks of pregnancy. A basal blood sample was collected from each of these women, in the morning, at the routine antenatal visit (38th week). A second blood specimen was collected at the end of a spontaneous labor, at vaginal delivery.

Group 2 comprised 11 primigravidas who were studied while undergoing cesarean delivery during spontaneous labor between the 39th and 40th weeks of pregnancy, because of failure to progress (dynamic dystocia). All patients had undergone from 3 to 5 hours of labor. A basal blood sample was collected at the routine antenatal visit (38th week).

Group 3 included 14 women (6 primigravidas and 8 multiparas) who were studied while undergoing elective cesarean delivery (repetitive surgery, podalic, or breech presentation). Blood samples were collected before surgery and immediately following fetal extraction.

All blood samples (4–6 mL) were collected in ice-chilled polypropylene tubes and centrifuged at 3200 rpm for 15 minutes at 4° C. Serum specimens were stored at −20° C. until assayed. Samples were not thawed before assaying.

Activin A levels were measured using a one-step (simultaneous) monoclonal antibody-based ELISA (2F8:6H5) as described in Romero et al., supra. Briefly, Nunc Immunolon Maxisorp microtiter plates were coated overnight (2F8, 4 μg/mL). Standard control diluted samples (1:5 or 1:1) and freshly diluted horseradish-peroxidase-conjugated secondary antibody were added in 20% normal human serum to each reagent/well and incubated for 2 hours at room temperature. The assay limit of detection was 200 pg/mL. The inter- and intra-assay coefficients of variation were 6.0 and 2.3%, respectively. The statistical analysis of the results was done by using analysis of variance.

Placental and membrane specimens were collected from pregnant women undergoing vaginal delivery (n=2) or elective cesarean delivery (n=3) at term. Placental chunks (1 cm thick) and membrane slices (0.4 cm thick) were immediately excised, cut, and rinsed in saline solution. Tissues were then fixed in 10% formalin for 5 hours at 4° C. and postfixed with the addition of 10% sucrose for three days at 4° C. Frozen sections were cut (20 μm) on a cryostat, mounted onto gelatin-poly-1-lysine-coated slides, and air dried.

The sections were rinsed in 2×NaCl/Na citrate and dehydrated in an ascending ethanol series and vacuum dried until hybridization. The specimens were hybridized for 30 minutes following a previously described in situ protocol (Woodruff et al., *Molec. Endocrinol.*, 1: 561–568 [1987]; Woodruff et al., *Science*, 239: 1296–1299 [1988]) and were acetylated with 0.25% acetic anhydride in 0.1M triethanolamine.

The ActRII cDNA was a 400-bp NarI to KpnI fragment from the mouse ActRII cDNA, which includes the entire extracellular domain. Mouse and human ActRII are greater than 95% identical. Mathews et al., *Cell*, 65: 973–982 (1991). Thus, the mouse probe is expected to hybridize at high stringency to human mRNA. The ActRIIB cDNA was a 550-bp SmaI fragment from the mouse ActRIIB cDNA, which includes the extracellular and transmembrane domains. Both fragments were cloned into the vector Bluescript SK (Stratagene) for generation of probes. To control for non-specific hybridization, adjacent sections were hybridized with sense-orientation probes. Sections of rat brain were used as positive hybridization controls.

Radioactive ($^{35}$S) cRNA probes were prepared by incubating 36 mM TRIS buffer (pH 7.5), 0.1 μg linearized plasmid in 6 mM MgCl$_2$, 2 mM spermidine, 8 m dithiothreitol (DTT), 25 mM UPT/GTP/CTP, 5 μM unlabeled GTP ($\alpha$-$^{35}$S) GTP, 1 U RNAsin, and 10 U SP6 polymerase for 60 minutes at 37° C. The specific activity of the probes was approximately $1.0 \times 10^8$ dpm/μg.

Each slide was hybridized using 100 μL of hybridization probe solution ($10^6$ cpm/mL) in a buffer containing 50% formamide, 10% dextran, 1×Denhardt's solution, 12 mM EDTA, 30 mM NaCl, 0.5 mL/mL yeast tRNA, and 10 mM DTT; slides were cover-slipped and incubated at 55° C. overnight. Once coverslips were removed, the slides were rinsed in 4×SSC, digested with RNAase A (20 μL/mL) for 30 minutes at 37° C., and rinsed sequentially in 2×, 1×, 0.5×, and 0.1×SSC.

Dehydrated sections were exposed to X-ray film for one day, dipped in NTB3 nuclear emulsion, exposed for 10 days, and developed.

Results

Activin A was detected in all maternal serum samples examined. The range of activin A serum levels at term was similar in all three groups evaluated (range 105 ng/mL vaginal delivery; 1–6 ng/mL cesarean delivery; 1–7 ng/mL elective cesarean). Activin A levels in maternal serum at vaginal delivery and at cesarean performed after spontaneous onset of labor were significantly higher than at term (p<0.01). No significant changes of activin A levels were observed before and after delivery in women undergoing elective cesarean delivery.

The most intense signal representing ActRIIB mRNA was in the syncytiotrophoblast layer of the placenta villi at term; rate granuli were positive in cytotrophoblast and mesenchymal cells. Hybridization of ActRII probes in placental villi was low. Some staining within the villi was noted. The signal was considered positive due to no localization of sense strand cRNAs in adjacent sections of human placenta.

The epithelial cells of the amnion layer intensely hybridized to the ActRIIB probe. Cells of the chorion and maternal decidua also hybridized intensely to labeled antisense strand ActRIIB mRNA probes. No difference in localization or intensity of activin receptor isotype mRNAs was noted in samples collected from vaginal delivery or from elective cesarean.

The present study demonstrates that maternal serum activin A levels increase in pregnant women undergoing vaginal delivery and cesarean delivery after spontaneous labor. Secondly, placenta, fetal membranes, and maternal decidua express activin receptor mRNA. The presence of spontaneous labor and not the manner of delivery is highly correlated to maternal serum activin A levels. In fact, maternal serum activin A levels increase 2–5 fold during vaginal delivery and 0.5–5 fold during cesarean delivery after spontaneous labor. By contrast, activin A levels do not change in patients following elective cesarean delivery.

EXAMPLE IV

Purified recombinant human follistatin is obtained by standard methods of recombinant expression as described by Esch et al., *Mol. Endocrinol.*, 1: 849–855 [(1987); Shimasaki et al., *Proc. Natl. Acad. Sci. USA*, 85: 4218–4222 (1988). It is produced as a sterile, endotoxin-free reagent. Human follistatin is administered every day for ten days to a 30-year old women in her 30th week of pregnancy who is experiencing early labor (stage 1), in an amount of two times the level of activin present in the serum of the women as of the day of treatment, as measured by ELISA of a blood sample. She does not deliver and continues her pregnancy.

Activin levels, uterine contractions, and cervical dilation are monitored. Once contractions have stopped and cervical dilation is not progressed, follistatin therapy is discontinued, but activin A serum concentration is still measured periodically to monitor for impending or imminent delivery.

What is claimed is:

1. A method for avoiding premature labor in a pregnant mammal comprising administering to said mammal during labor, but before an infant is to be delivered, an effective amount of an activin antagonist.

2. The method of claim 1 wherein the mammal is a non-human primate or a human.

3. The method of claim 2 wherein the mammal is a human and the activin antagonist is human follistatin or a humanized antibody to activin.

4. The method of claim 1 wherein the activin antagonist is an activin A antagonist.

5. The method of claim 1 wherein the activin antagonist is follistatin.

6. The method of claim 1 wherein the activin antagonist is an anti-activin antibody.

7. The method of claim 1 wherein the activin antagonist is a soluble form of the activin receptor.

8. The method of claim 1 wherein the activin antagonist is administered to the mammal during the period of dilation of the os uteri of the mammal.

9. A method for assaying whether a pregnant mammal is in imminent delivery of its fetus in preterm labor comprising contacting a maternal serum sample or amniotic fluid sample of the mammal with a reagent that detects activin A and measuring the level of activin A in the serum or amniotic fluid.

10. The method of claim 9 wherein the reagent is a labeled antibody that binds to activin A.

11. The method of claim 9 wherein the reagent is labeled follistatin.

12. The method of claim 9 wherein the contacting is done using an ELISA assay.

13. The method of claim 9 wherein the contacting is done using a RIA assay.

14. The method of claim 9 wherein amniotic fluid is assayed.

15. The method of claim 9 wherein serum is assayed.

16. A method for avoiding premature labor in a pregnant mammal comprising contacting a maternal serum sample or amniotic fluid sample of the mammal with a reagent that detects activin A; measuring the level of activin A in the serum or amniotic fluid; and if the measurement of activin A levels indicates that preterm labor is imminent or is occurring, administering to said mammal during labor, but before an infant is to be delivered, an effective amount of an activin antagonist to avoid premature labor in the mammal.

* * * * *